United States Patent [19]
Spruce et al.

[11] Patent Number: 6,004,933
[45] Date of Patent: Dec. 21, 1999

[54] CYSTEINE PROTEASE INHIBITORS

[75] Inventors: Lyle W. Spruce, Chula Vista, Calif.; Albert C. Gyorkos, Westminster; John C. Cheronis, Conifer, both of Colo.; Val S. Goodfellow, Tucson, Ariz.; Axel H. Leimer, Westborough, Mass.; John M. Young, Redwood City, Calif.; James Ivan Gerrity, Albany, Oreg.

[73] Assignee: Cortech Inc., Bedminster, N.J.

[21] Appl. No.: 09/065,258

[22] Filed: Apr. 23, 1998

Related U.S. Application Data

[60] Provisional application No. 60/044,819, Apr. 25, 1997.
[51] Int. Cl.$^6$ .......................... A61K 38/03; C07D 215/02; C07D 237/30; C07D 239/70; C07D 241/36; C07D 253/10
[52] U.S. Cl. .................. 514/17; 514/18; 514/19; 514/213; 514/221; 514/243; 514/249; 514/255; 514/259; 514/299; 514/315; 514/387; 540/523; 544/182; 544/237; 544/240; 544/242; 544/298; 544/354; 544/358; 546/164; 548/125; 548/484; 436/86; 436/90
[58] Field of Search ..................... 548/125, 484, 548/17; 514/17, 18, 19, 213, 249, 259, 299, 387; 540/523; 544/182, 237, 240, 298, 354, 358; 546/164

[56] References Cited

U.S. PATENT DOCUMENTS

| | | | |
|---|---|---|---|
| 5,618,792 | 4/1997 | Gyorkos et al. | 514/18 |
| 5,760,048 | 4/1996 | Wang et al. | 514/290 |

*Primary Examiner*—Johann Richter
*Assistant Examiner*—Taofiq A. Solola
*Attorney, Agent, or Firm*—Dechert Price & Rhoads

[57] ABSTRACT

The present invention relates to cysteine protease inhibitors of the general formula (I):

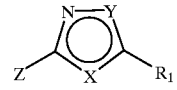

wherein Z is a cysteine protease binding moiety; X and Y are S, O or optionally substituted N; and $R_1$ is optionally substituted alkyl or aryl.

146 Claims, 3 Drawing Sheets

CYSTEINE PROTEASE INHIBITORS

This application claiming benefit of provisional application Ser. No. 60/044,819 filed Apr. 25, 1997.

BACKGROUND OF THE INVENTION

Numerous cysteine proteases have been identified in biological systems. A "protease" is an enzyme which degrades proteins or peptides into smaller components. The term "cysteine protease" refers to proteases which are distinguished by the presence of a cysteine residue which plays a critical role in the catalytic process. Mammalian systems, including humans, normally degrade and process proteins via a variety of mechanisms including the actions of cysteine proteases. However, when present at elevated levels or when abnormally activated, or where introduced into a biological system in the context of a viral, bacterial or parasitic infection, cysteine proteases are thought to be involved in numerous pathophysiological processes and disease states.

For example, calcium-activated neutral proteases ("calpains") comprise a family of intracellular cysteine proteases which are ubiquitously expressed in mammalian tissues. Three major calpains have been identified: calpain I and II, and p94. The calpain family of cysteine proteases has been implicated in many diseases and disorders, including stroke, neurodegeneration, such as Alzheimer's disease, amyotrophy and motor neuron damage; acute central nervous system injury, muscular dystrophy, bone resorption, platelet aggregation, cataracts and inflammation. Calpain I has been implicated in excitatory amino-acid induced neurotoxicity disorders including ischemia, hypoglycemia and epilepsy. The cysteine protease p94, a muscle-specific member of the calpain family, has been identified as a gene product responsible for limb girdle muscular dystrophy (Barrett A. J., et al. *ICOP Newsletter,* 1–2 (1996)).

Lysosomal cysteine proteases or cathepsins (including cathepsins B, C, H, L, S, O and O2/K) belong to the papain superfamily of cysteine proteases. They are widely distributed and differentially expressed among tissues. Intracellularly, they serve a variety of digestive and processing functions. Extracellularly, they may be involved in tissue remodeling and in pathologies such as arthritis, inflammation, myocardial infarction, Alzheimer's disease, cancer and muscular dystrophy (Elliott E., et al., *Per. in Drug Disc. and Des.,* 6:12–32 (1996)).

Interleukin-1β converting enzyme ("ICF") is a member of the caspase family of cysteine proteases which catalyzes the formation of interleukin-1β (IL-1β), as well as the formation of interferon-γ inducing factor (IGIF) from their inactive precursors, proIL-1β and pro-IGIF, respectively. Interleukin-1β is an immunoregulatory protein implicated in inflammation, diabetes, septic shock, rheumatoid arthritis and Alzheimer's disease. ICE and/or other caspases have also been linked to the apoptotic cell death of neurons which is implicated in a variety of neurodegenerative disorders including Parkinson's disease, ischemia and amyotrophic lateral sclerosis (ALS)(Dinarello C., et al., *New Eng. J. Med.,* 328: 106–113 (1993)).

Cysteine proteases are also produced by various viral pathogens and appear to be involved in every stage of reproduction including DNA and RNA translation and synthesis, and capsid formation (Gorbalenya A., et al., *Per. In Drug Disc.,* 6:64–86 (1996); Krausslich et al., *Ann. Rev. Biochem.,* 57:701–54 (1988)). Examples of viral pathogens include Picornaviridae, which includes the genera Enterovirus, Rhinovirus, Cardiovirus, and Aphthovirus, which cause numerous human disease syndromes, ranging from fatal paralysis, encephalitis, meningitis, hepatitis and myocarditis to the common cold (Krausslich et al., *Ann. Rev. Biochem.,* 57:701–54 (1988)). The picornaviral 3C proteinases, which are produced by all picornaviruses, are responsible for processing viral polyproteins, an essential stage in viral growth (Malcolm B., et al. *Biochemistry,* 34:8172–8179 (1995)).

In addition, parasitic cysteine proteinases play significant roles in host-parasite interactions and pathogenesis (Robertson C., et al., *Pers. in Drug Disc. and Des.,* 6:99–118 (1996)). For example, most of the proteinase activity detected in trypanosomes and various Leishmania species has been characterized as belonging to the cysteine protease class. Other proteases are produced by Clostridium histolyticum and malaria parasites, such as Plasmodium falciparum and Plasmodium vinckei strains, and Schistosoma.

Cancer procoagulant, CP, a cysteine proteinase from malignant cells, has emerged as a probable activator of the coagulation system in cancer (Alessio M. G., et al., *Eur. J Haematol,* 45: 78–81 (1990); Gordon S., *Methods in Enz.,* 244:568–581 (1994); Gordon S., *Sem. in Thromb. and Hemo.,* 18,4:424–433 (1992)).

Existing cysteine protease inhibitors are primarily irreversible in nature; only weakly inhibit the enzymatic activity of the targeted protease and/or are toxic. Thus, there is a need for effective inhibitors of cysteine proteases as therapeutic and as prophylactic agents for the treatment and/or prevention of cysteine protease mediated pathologies.

SUMMARY OF THE INVENTION

The present invention relates to cysteine protease inhibitors of the general formula (I):

wherein Z is a cysteine protease binding moiety, Z being a carbonyl containing group, preferably an amino carbonyl containing group, wherein the carbon of the heterocycle is attached directly to the carbonyl group of Z.

In the above formula (I), $R_1$ is alkyl or alkenyl optionally substituted with 1–3 halo or hydroxy; alkylamino, dialkylamino, alkyldialkylamino; or cycloalkyl, alkylcycloalkyl, alkenylcycloalkyl, ($C_5$–$C_{12}$)aryl, ($C_5$–$C_{12}$) arylalkyl or ($C_5$–$C_{12}$)arylalkenyl optionally comprising 1–4 heteroatoms selected from N, O and S, and optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamide, ($C_5$–$C_6$)aryl, —O—($C_5$–$C_6$)aryl, arylcarboxamide, alkylthio or haloalkylthio; and X and Y are independently O, S or N, where N is optionally substituted with alkyl or alkenyl optionally substituted with 1–3 halo atoms; ($C_5$–$C_6$)aryl, arylalkyl or arylalkenyl optionally comprising 1–3 heteroatoms selected from N, O and S, and optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamide, arylcarboxamide, alkylthio or haloalkylthio; provided that at least one of Y or X is N. It will be understood that where Y or X is substituted nitrogen, both Y and X must be nitrogen.

In one embodiment, $R_1$ is methyl, dimethylamino, phenyl or benzyl optionally substituted with methyl, halo, methylenedioxy, methoxy, dimethoxy, trimethoxy, trifluoromethyl and dimethylamino.

According to several preferred embodiments, X is O and Y is N; X is N and Y is O; or both X and Y are N.

Typically Z comprises 1 to 5 amino acid residues or mimetics thereof. Thus, Z may, for example, comprise a pentapeptidyl, tetrapeptidyl, tripeptidyl or dipeptidyl binding moiety.

According to a preferred embodiment, Z is of the formula (II):

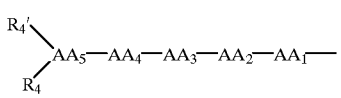
(II)

wherein $AA_1$, $AA_2$, $AA_3$, $AA_4$ and $AA_5$ are independently an amino acid residue or amino acid residue mimetic; a direct bond or absent; and $R_4$ and $R_4'$ are independently —C(O)$R_5$, —C(O)NH$R_5$, —S(O)$_2R_5$, —C(O)O$R_5$, —C$R_5$ or $R_5$, where $R_5$ is H, alky, alkenyl or alkynyl optionally substituted with halo, cyano, nitro, haloalkyl, amino, aminoalkyl, dialkylamino, haloalkoxy, carboxyl, carboalkoxy or alkylcarboxamide; cycloalkyl, alkylcycloalkyl, ($C_5$–$C_{12}$) aryl or ($C_5$–$C_{12}$) arylalkyl optionally comprising 1–4 heteroatoms selected from N, O and S, and optionally substituted with halo, cyano, nitro, haloalkyl, amino, aminoalkyl, dialkylamino, haloalkoxy, carboxyl, carboalkoxy, alkylcarboxamide, alkyl, alkenyl, alkynyl or ($C_5$–$C_{12}$)aryl; or absent; or together $R_4$ and $R_4'$ form a ring comprising 5–7 atoms selected from C, N, S and O. Typical terminal $R_4$ groups include Cbz, succinic acid derivatives of the formulas —C(O)CH(—CH$_2$CH(CH$_3$)$_2$)CH$_2$COOH, —C(O)CH$_2$CH$_2$COOH, and —C(O)CH$_2$CH$_2$C(O)OC(CH$_3$)$_3$; toluenesulfonyl, methane sulfonyl, FMOC, (t)-menthyloxy-CO— and acetyl.

Preferably, the amino acids are selected from arginine or an arginine mimetic, proline; aspartic and glutamic acid and the aryl and alkyl esters thereof; alanine and glycine optionally substituted at the α-carbon or α-nitrogen with alkyl, cycloalkyl or aryl; leucine, isoleucine; cysteine optionally substituted at the sulfur atom with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxarnide, alkylthio or haloalkylthio; phenylalanine, homophenylalanine, dehydro-phenylalanine, indoline-2-carboxylic acid; tetrahydroisoquinoline-2-carboxylic acid optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkyltlio or haloalkylthio; tyrosine, serine or threonine optionally substituted with alkyl or aryl; tryptophan, histidine, methionine, valine, norvaline, norleucine, octahydroindole-2-carboxylic acid; asparagine, glutamine and lysine optionally substituted at the nitrogen atom with alkyl, alkenyl, alkynyl, alkoxyalkyl, alkylthioalkyl, alkylaminoalkyl, dialkylaminoalkyl, carboxyalkyl, alkoxycarbonyl alkyl or cycloalkyl, bicycloalkyl, cycloalkyl alkyl, bicycloalkyl alkyl or fused aryl-cycloalkyl alkyl optionally comprising 1 or more heteroatoms selected from N, O and S.

Alternatively, $AA_1$ is of the formula (IIIa):

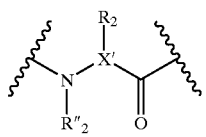
(IIIa)

wherein X' is $CR_2'$ or N; and $R_2$, $R_2'$ and $R_2''$ are independently H; alkyl or alkenyl optionally substituted with 1–3 halo, hydroxy, thio, alkylthio, amino, alkylamino, dialkylamino, alkylguanidinyl, dialkylguanidinyl, guanidinyl; 'RCOR', —RCOOR', —RNR'R"R° or —RC(O)NR'R" where R is alkyl or alkenyl, and R', R" and R° are independently H, alkyl, alkenyl, cycloalkyl or ($C_5$–$C_6$)aryl; or cycloalkyl, alkylcycloalkyl, alkenylcycloalkyl, alkyl-oxyaryl, alkylthioaryl, ($C_5$–$C_{12}$) aryl, ($C_5$–$C_{12}$)arylalkyl or ($C_5$–$C_{12}$) arylalkenyl optionally comprising 1–4 heteroatoms selected from N, O and S, and optionally substituted with hydroxy, halo, cyano, nitro, haloalkyl, amino, aminoalkyl, dialkylamino, amidine, alkylamidine, dialkylamidine, alkyl, alkenyl, alkynyl, alkoxy, haloalkoxy, carboxyl, carboalkoxy, alkylcarboxamide, ($C_5$–$C_6$)aryl, —O—($C_5$–$C_6$)aryl, arylcarboxamide, alkylthio or haloalkylthio; or $R_2$ and $R_2'$ together with X' form a ring comprising 4–7 atoms selected from C, N, S and O, said ring optionally subsitituted with hydroxy, halo, cyano, nitro, haloalkyl, amino, aminoalkyl, dialkylamino, amidine, alkylamidine, dialkyl amidine, alkyl, alkenyl, alkynyl, alkoxy, haloalkoxy, carboxyl, carboalkoxy, alkylcarboxamide, ($C_5$–$C_6$)aryl, —O—($C_5$–$C_6$)aryl, arylcarboxamide, alkylthio or haloalkylthio.

$AA_2$ may be a residue of the formula (IIIb):

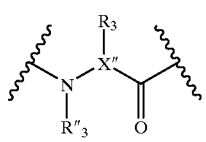
(IIIb)

or selected from a residue mnimetic of formulas IV to XXIV:

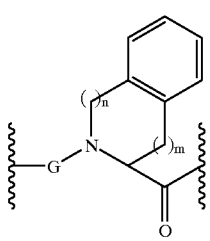
(IV)

(V) 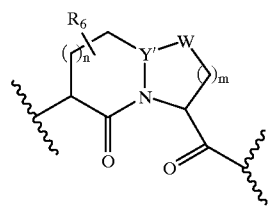
(VI) 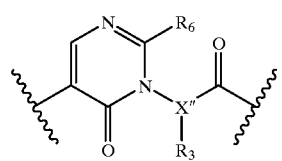
(VII) 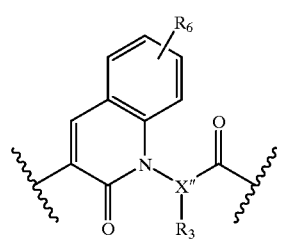
(VIII) 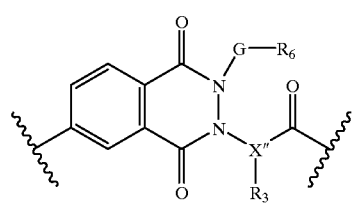
(IX) 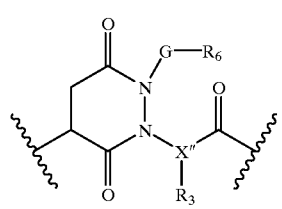
(X) 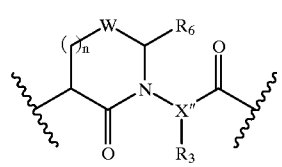
(XI) 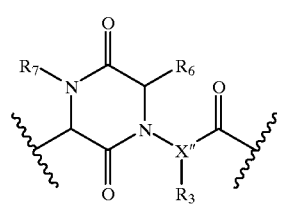
(XII) 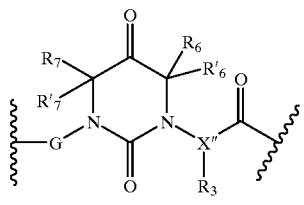
(XIII) 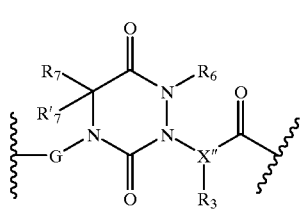
(XIV) 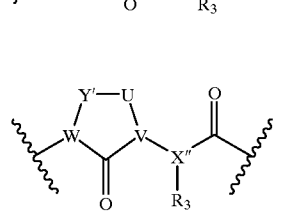
(XV) 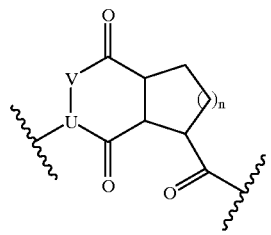
(XVI) 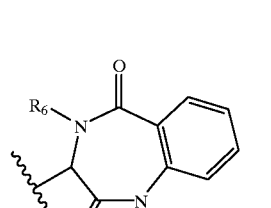
(XVII) 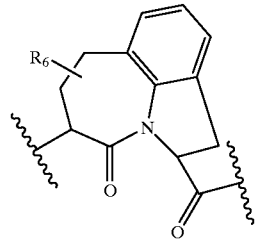

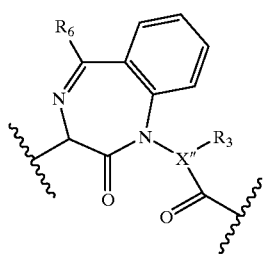
(XVIII)

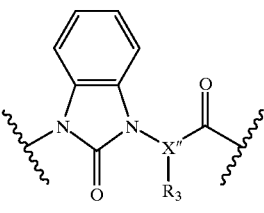
(XXIV)

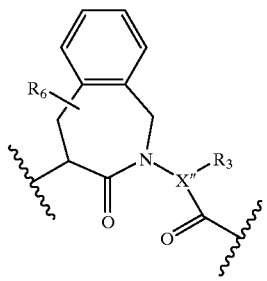
(XIX)

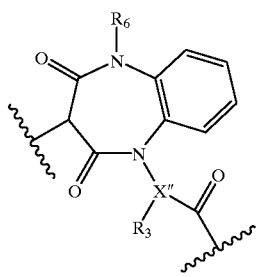
(XX)

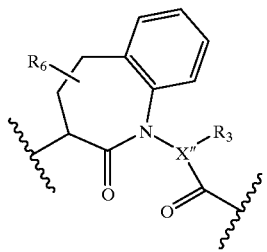
(XXI)

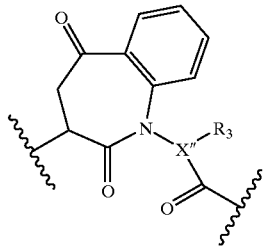
(XXII)

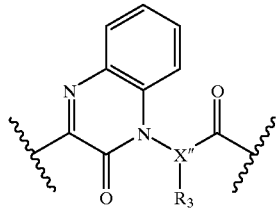
(XXIII)

wherein X" is CR'$_3$ or N;

R$_3$, R'$_3$ and R"$_3$ are independently H; alkyl or alkenyl optionally substituted with 1–3 halo, hydroxy, thio, alkylthio, amino, alkylamino, dialkylamino, alkylguanidinyl, dialkylguanidinyl, guanidinyl; —RCOR', —RCOOR' or —RC(O)NR'R" where R is alkyl or alkenyl, and R' and R" are independently H, alkyl, alkenyl, cycloalkyl or (C$_5$–C$_6$)aryl; or cycloalkyl, alkylcycloalkyl, alkenylcycloalkyl, alkyl-oxyaryl, alkyl-thioaryl, (C$_5$–C$_{12}$) aryl, (C$_5$–C$_{12}$)arylalkyl or (C$_5$–C$_{12}$)arylalkenyl optionally comprising 1–4 heteroatoms selected from N, O and S, and optionally substituted with hydroxy, halo, cyano, nitro, haloalkyl, amino, aminoalkyl, dialkylamino, amidine, alkylamidine, dialkylamidine, alkyl, alkenyl, alkynyl, alkoxy, haloalkoxy, carboxyl, carboalkoxy, alkylcarboxamide, (C$_5$–C$_6$)aryl, —O—(C$_5$–C$_6$)aryl, arylcarboxamide, alkylthio or haloalkylthio;

m is 0, 1 or 2;

n is 0, 1 or 2;

G is —C(O)—, —NHC(O)—, —S(O)$_2$—, —OC(O)—, —C— or a direct bond;

R$_6$, R$_7$, R'$_6$, R'$_7$ are independently H, alkyl, alkenyl, halo, alkoxy, carboxyl, carboalkoxy, amino, aminoalkyl, dialkylamino; cycloalkyl, (C$_5$–C$_6$) aryl or (C$_5$–C$_6$) arylalkyl optionally comprising 1–3 heteroatoms selected from N, O and S, and optionally substituted with alkyl, alkenyl, alkynyl, halo, cyano, nitro, haloalkyl, haloalkoxy, amino, alkylamino, dialkylamino, alkoxy, haloalkoxy, carboxyl, carboalkoxy, alkylcarboxamide, alkylthio, guanidine, alkylguanidine, dialkylguanidine, amidine, alkylamidine or dialkylamidine; and U, V, W and Y' are independently or together N, C, C(O), N(R$_9$) where R$_9$ is H, alkyl, halo, alkoxy, carboalkoxy, cycloalkoxy, carboxyl, alkylthio, amino, alkylamino, dialkylamino, or aryl, fused aryl or cycloalkyl optionally comprising 1 or more heteroatoms selected from O, S and N, and optionally subsituted with halo or alkyl; N(R$_{10}$) where R$_{10}$ is H, alkyl, alkenyl or cycloalkyl, aryl, arylalkyl or fused aryl-cycloalkyl optionally comprising 1–4 heteroatoms selected from N, O and S, and optionally substituted with alkyl, alkenyl, alkynyl, halo, cyano, nitro, haloalkyl, haloalkoxy, amino, alkylamino, dialkylamino, alkoxy, haloalkoxy, carboxyl, carboalkoxy, alkylcarboxamide, alkylthio, guanidine, alkylguanidine, dialkylguanidine, amidine, alkylamidine or dialkylamidine; or C(R$_{11}$)(R$_{12}$) where R$_{11}$ and R$_{12}$ are independently or together H, alkyl, alkytlio, alkythioalkyl or cycloalkyl, alkylcycloalkyl, phenyl or phenyl alkyl optionally subsituted with guanidine, carboalkoxy, hydroxy, haloalkyl, alkylthio, alkylguanidine, dialkylguanidine, amidine, alkylamidine or dialkylamidine.

In a preferred embodiment, X' and X" are C, and R'$_2$ and R'$_3$ are H.

In another embodiment, X' and/or X" are N.

Where Z is a calpain binding moiety, preferably R$_2$ is benzyl optionally substituted with alkoxy; H$_2$NC(=$^+$NH$_2$)NHCH$_2$CH$_2$CH$_2$—; —R'—C(=$^{30}$ NH$_2$)NH$_2$; —R'—NHC ($=^+$NR")NR°; or —R'—NR"R° where R' is cycloalkyl, aryl or arylalkyl optionally substituted with one or more heteroatoms selected from N, S or O; and R" and R° are alkyl or cycloalkyl; or $CH_3SCH_2CH_2$—, $HOOC(CH_2)_2CH_2$—, cyclohexyl-$CH_2$—, imidazolyl-$CH_2$, benzyl optionally substituted with OH or —O-benzyl, $(CH_3)_2CHCH_2$—, $(CH_3)_2CH$—, $CH_3CH_2CH_2$— or $CH_3(CH_2)_2CH_2$—; and $R_3$ is —$CH_2$-benzyl, benzyl, $(CH_3)_3C$—, $(CH_3)_3CCH_2$—, $(CH_3)_2CH$—, $CH_3(CH_2)_2CH_2$—, $CH_3CH_2CH(CH_3)$— or $(CH_3)_2CHCH_2$—. Preferably, $R_5$ is benzyl, isoquinolinyl, quinolinyl, naphthyl or $HOOCCH_2C(CH_2CH(CH_3)_2)$—; or $R_4$ is Cbz wherein the phenyl is optionally substituted with nitro. Additionally, $R_4$ may be toluenesulfonyl, methanesulfonyl, FMOC or (+)-menthyl-oxy-CO—.

In one embodiment, $AA_3$ is leucine, $AA_4$ and $AA_5$ are direct bonds or absent, and $R_5$ is alkyl.

Several particular embodiments include those where Z is
$R_4$—Leu—Leu—Leu—;
$R_4$—Leu—Leu—;
$R_4$—Leu—Leu—Phe—;
$R_4$—Leu—Abu—;
$R_4$—Val—Phe—;
$R_4$—Leu—Leu—Nle—;
$R_4$—Ala—t—BuGly—Val—$R_4$-t-BuGly—Val—$R_4$—Leu—Leu—Met—; or
R4—Leu—Nle—.

Preferably, Z is Cbz—Leu—Nle—; or Cbz—Leu—Val—.

Z may also be a cysteine cathepsin binding moiety, where preferably $R_2$ is $CH_3$—, $(CH_3)_2CH$—, $(CH_3)_2CHCH_2$—, $CH_3(CH_2)_2CH_2$—, $H_2NC(=^+NH_2)NHCH_2CH_2CH_2$—; —R'—C($=^+NH_2$)$NH_2$; —R'—NHC($=^+$NR")NR°; or —R'—NR"R° where R' is cycloalkyl, aryl or arylalkyl optionally substituted with one or more heteroatoms selected from N, S or O; and R" and R° are alkyl or cycloalkyl; benzyl or —$CH_2$-benzyl optionally substituted with OH or —OR' where R' is alkyl or aryl; $CH_3CH$(—O-benzyl)— or benzyl-S—$CH_2$—; and $R_3$ is H, $(CH_3)_2CH$—, $(CH_3)_2CHCH_2$—, $CH_3(CH_2)_2CH_2$—, $H_2N(CH_2)_3CH_2$—, $H_2N(CH_2)_2CH_2$—, $H_2NC(=^+NH_2)NHCH_2CH_2CH_2$—; —R'—C($=^+NH_2$)$NH_2$; —R'—NHC($=^+$NR")NR°; or —R'—NR"R° where R' is cycloalkyl, aryl or arylalkyl optionally substituted with one or more heteroatoms selected from N, S or O; and R" and R° are alkyl or cycloalkyl; benzyl, benzyl substituted with hydroxy and halo; or (naphthyl)-$CH_2$—.

In one embodiment, Z is a cathepsin B binding moiety, where preferably, $R_2$ and $R_3$ are independently benzyl, —$CH_2$-benzyl, $H_2NC(=^+NH_2)NHCH_2CH_2CH_2$—; —R'—C($=^+NH_2$)$NH_2$; —R'—NHC($=^+$NR")NR°; or —R'—NR"R° where R' is cycloalkyl, aryl or arylalkyl optionally substituted with one or more heteroatoms selected from N, S or O; and R" and R° are alkyl or cycloalkyl; $H_2N(CH_2)_3CH_2$— or $H_2N(CH_2)_2CH_2$—; and preferably $AA_3$ is Ile, Leu, absent or a direct bond.

According to a particular embodiment, —$AA_2$—$AA_1$— are selected from:
—Phe—hPhe—;
—Arg—hPhe—;
—Arg mimetic—hPhe—;
—Leu—hPhe—; and
—Omr—hPhe.

Z may be a cathepsin L binding moiety, where $R_3$ is preferably benzyl or $(CH_3)_2CHCH_2$—; and $R_2$ is —$CH_2$-benzyl.

Where Z is a cathepsin S binding moiety; preferably $R_2$ and $R_3$ are alkyl; more preferably $(CH_3)_2CH$—, $(CH_3)_2CHCH_2$— or $CH_3(CH_2)_2CH_2$—.

In another embodiment, $R_3$ is benzyl, $(CH_3)_2CHCH_2$— or $(CH_3)_2CH$—; and $R_2$ is —$CH_2$-benzyl. According to one particular embodiment, $AA_3$, $AA_4$ and $AA_5$ are direct bonds or absent; $R_5$ is benzyl, isoquinolinyl, quinolinyl, naphthyl or $HOOCCH_2C(CH_2CH(CH_3)_2)$—; or $R_4$ is Cbz.

Where Z is a cathepsin H binding moiety; Z is preferably
$R_4$—hPhe—; or
HCl•hPhe—.

Z may also be a cathepsin K binding moiety; where preferably $R_3$ is benzyl, $(CH_3)_2CHCH_2$— or $(CH_3)_2CH$—; and preferably $AA_3$ is Gly; and $AA_4$ is Val or D—Val.

In another embodiment,
$AA_1$ is Arg, Arg mimetic or hPhe;
$AA_2$ is Pro;
$AA_3$ is Gly; and
$AA_4$ is Val or D—Val; or preferably Z is
$R_4$—Pro—$AA_1$—;
$R_4$—Gly—Pro—$AA_1$—;
$R_4$—Val—Gly—Pro—$AA_1$—;
D—Val—Gly—Pro—$AA_1$—; or
$R_4$—D—Val—Gly—Pro—$AA_1$; where $AA_1$ is Apa, Arg or Arg mimetic, or hPhe.

Other embodiments include compounds where Z is
$R_4$—$AA_3$—Leu—hPhe—;
$R_4$—$AA_3$—Phe—hPhe—; or
$R_4$—$AA_3$—Val—hPhe—; where $AA_3$ is Gly, Val, D—Val, a direct bond or absent.

Where Z is a caspase binding moiety; preferably $R_2$ is —RCOOR'; where preferably R is —$CH_2$— and preferably R' is H; where preferably $AA_3$ and $AA_4$ are amino acid residues and $AA_5$ is a direct bond.

Where Z is an interleukin-1β converting enzyme binding moiety; $AA_4$ may be optionally substituted tyrosine or leucine; $AA_3$ may be valine, glutamate or an ester of glutamate; and $R_3$ may be —$CH_3$ or $(CH_3)_2CH$—.

In another embodiment, $R_3$ is —$CH_3$ or imidazolyl-$CH_2$—; $AA_3$ is valine or glutamate; and $R_5$ is —$CH_3$.

Z may also be $R_4$—$AA_5$—$AA_4$—$AA_3$—Pro—$AA_1$; where $AA_1$ is Asp or Asp ester; where —$AA_5$— $AA_4$— $AA_3$— may be —Ala—; —Glu—; —Val—; —Tyr—Ala—; —Tyr—Glu—; —Tyr—Val—; —Leu—Ala—; —Leu—Glu—; or —Leu—Val—.

In yet a further embodiment where Z is an interleukin-1β converting enzyme binding moiety, $AA_2$ is of the formula (VI);

wherein X" is $CR'_3$ where preferably $R'_3$ is H; and
$R_2$ is —RCOOR' where R is alkyl or alkenyl, and R' is H, alkyl, alkenyl, cycloalkyl or $(C_5-C_6)$ aryl. In another, $AA_4$ and $AA_5$ are direct bonds or absent, $AA_3$ is Tyr or Tyr(O—R') or a direct bond or absent; $R_2$ is —RCOOR' where R is alkyl or alkenyl, and R' is H, alkyl, alkenyl, cycloalkyl or $(C_5-C_6)$ aryl; $R_6$ is phenyl or benzyl substituted with halo; and $R_5$ may be benzyl, isoquinolinyl, quinolinyl, naphthyl or $HOOCCH_2C(CH_2CH(CH_3)_2)$—.

Where Z is a YAMA binding moiety, preferably $R_2$ is —RCOOR' where preferably R is —$CH_2$— and $AA_4$ is Asp or an ester thereof In another embodiment, $AA_3$ is optionally substituted glutamine or glutamic acid or an ester thereof. In yet another embodiment $R_2$ is $(CH_3)_2CH$— or $CH_3SCH_2CH_2$—.

Where Z is a FLICE binding moiety, preferably $R_2$ is —RCOOR', where preferably R is —$CH_2$—; $AA_4$ is optionally substituted lysine; and preferably $AA_3$ is glutamic acid; and $R_3$ is $(CH_3)_2CH$—.

Z may also be a viral or microbial cysteine protease binding moiety. In one embodiment, Z is a gingipain binding moiety. Where Z is a gingipain K binding moiety; $R_2$ is preferably —RNR'R"R° where preferably R is $(C_1–C_4)$ alkyl; R' is H; and preferably R" and R° are H or $(C_1–C_3)$ alkyl. In one embodiment $R_2$ is $^+H_3N(CH_2)_3CH_2$—. Where Z is a gingipain R binding moiety, preferably $R_2$ is $H_2NC(=^+NH_2)NHCH_2CH_2CH_2$—; —R'—C(=$^+NH_2$)$NH_2$; —R'—NHC(=$^+NR$")NR°; or —R'—NR"R° where R' is cycloalkyl, aryl or arylalkyl optionally substituted with one or more heteroatoms selected from N, S or O; and R" and R° are alkyl or cycloalkyl.

According to one embodiment, $AA_2$ is proline, where Z is $R_4$—Leu—Pro—$AA_1$—, where $AA_1$ is arginine or an arginine mimetic.

Z may also be a human coronavirus protease binding moiety, where preferably $R_2$ is $H_2NC(=^+NH_2)NHCH_2CH_2CH_2$—; —R'—C(=$^+NH_2$)$NH_2$; —R'—NHC(=+NR")NR'; or —R'—NR"R° where R' is cycloalkyl, aryl or arylalkyl optionally substituted with one or more heteroatoms selected from N, S or O; and R" and R° are alkyl or cycloalkyl; and preferably $R_3$ is $(CH_3)_2CH$—, $(CH_3)_2CHCH_2$— or $CH_3(CH_2)_2CH_2$—; $AA_3$ is Asp or ester thereof, Leu, Arg or Arg mimetic, or direct bond; $AA_4$ and $AA_5$ are direct bonds or absent; and $R_5$ is alkyl.

Where Z is a hepatitis A virus 3C proteinase binding moiety, $R_2$ is preferably —RC(O)NR'R" where R' and R" are H or —$CH_3$; or RCOOR' where R' is $CH_3$; and $AA_3$ and $AA_4$ are amino acid residues. Preferably, $AA_4$ is Leu; $R_3$ is —$CH_3$ and $AA_3$ is Ala.

Z may also be a hepatitis A virus 3C proteinase binding moiety, where Z is $R_4$—Leu—$AA_3$—Thr—Gln—;

$R_4$—Trp—$AA_3$—Thr—Gln—;

$R_4$—Val—$AA_3$—Thr—Gln—;

$R_4$—Ile—$AA_3$—Thr—Gln—; or $R_4$—D—Leu—$AA_3$—Thr—Gln—; where $AA_3$ is Arg or Arg mimetic.

Where Z is an Ad2 23K protease binding moiety, $R_2$ and $R_3$ are preferably H; $AA_3$ is alanine; $AA_4$ is leucine; $AA_5$ is a direct bond; and $R_4$ is absent.

Where Z is a human rhinovirus 3C protease binding moiety, preferably $R_2$ is RCOOR' where R is —$CH_2$—; $R_3$ is benzyl; and $AA_3$ is leucine, isoleucine or a direct bond.

In yet a further embodiment, $R_2$ is —RC(O)NR'R" where R' and R" are H, —$CH_3$ or —$CH_2CH_3$; or RCOOR' where R' is —$CH_3$ or —$CH_2CH_3$.

Z may also be a human picomain 2A protease; where $R_3$ is —CH(OR')$CH_3$ where R' is H, alkyl or aryl; and preferably $R_2$ is a hydrophobic side chain. Alternatively, $AA_1$ is Val or dehydro-Phe; $AA_2$ is Pro; and $AA_3$ is Val. Examples include compounds CE-2072, CE-2060 and CE-2061, the structures of which are shown below.

In another embodiment, Z is $R_4$—Ala—Ala—Pro—Val—; or $R_4$—Ala—Ala—Pro—Ala—.

Additionally, Z may be a protozoan protease binding moiety, such as a Trypanosoma, Leishmania or Schistosoma protease binding moiety. The protease may be a cathepsin L- or cathepsin B-like protease. In one embodiment, $R_2$ is $H_2N(CH_2)_3CH_2$—, $H_2NC(=^+NH_2)NHCH_2CH_2CH_2$—; —R'—C(=$^+NH_2$)$NH_2$; —R'—NHC(=$^+NR$")NR°; or —R'—NR"R° where R' is cycloalkyl, aryl or arylalkyl optionally substituted with one or more heteroatoms selected from N, S or O; and R" and R° are alkyl or cycloalkyl; —$CH_2$-benzyl or benzyl optionally substituted with OH; and preferably $R_3$ is benzyl, $(CH_3)_2CHCH_2$- or $(CH_3)_2CH$—; and $AA_3$ is Phe, Leu, Pro or a direct bond. In one example, $R_4$ is Boc or Suc.

Z may be also selected from —Pro—Phe—Arg—; —Phe—Arg—;—Val—Leu—Lys—; —Leu—Val—Tyr—; Suc—Leu—Tyr— or —Phe—Ala—.

Where Z is a Plasmodium protease binding moiety, preferably $R_2$ is $(CH_3)_2CH$—, —$CH_2$— benzyl, benzyl or phenyl optionally substituted with hydroxyl; $H_2NC(=^+NH_2)NHCH_2CH_2CH_2$—; —R'—C(=$^+NH_2$)$NH_2$; —R'—NHC(=$^+NR$")NR°; or —R'—NR"R° where R' is cycloalkyl, aryl or arylalkyl optionally substituted with one or more heteroatoms selected from N, S or O; and R" and R° are alkyl or cycloalkyl; or —R'—N(R")(R°) where R' is alkyl, and R" and R° are alkyl or cycloalkyl; or alkylimidazoyl; and $R_3$ is benzyl, $(CH_3)_2CHCH_2$—, $(CH_3)_2CH$—, $HOCH_2$— or —$CH_2OR'$.

In one embodiment, Z is $R_4$—Phe—Arg—;

$R_4$—Phe—(arginine mimetic)—;

$R_4$—Phe—Lys—;

$R_4$—Leu—hPhe—;

$R_4$—Val—Leu—Arg—;

$R_4$—Phe(e-Z)—Lys—;

$R_4$—Val—Leu—(Arg mimetic)—

$R_4$—Phe—Val—; or $R_4$—Phe—Ser(OBzl)—.

In another embodiment, Z is $R_4$—Phe—$AA_1$—; or $R_4$—Leu—$AA_1$—; where $AA_1$ is optionally substituted lysine; and where $R_4$ may be morpholino. In a further embodiment, $AA_3$, $AA_4$ and $AA_5$ are direct bonds or absent, and $R_4$ is Cbz.

The present invention also provides methods of inhibiting the enzymatic activity of one or more cysteine proteases comprising contacting a protease with an inhibitory amount of a compound described herein.

Preferably the compound is selected from [2-[5-(3-methylbenzyl)-1,3,4-oxadiazolyl]carbonyl]-2-(S)-methylpropyl]-L-phenylalanamide-(3R)-(isobutyl)succinic acid;

Acetyl-L-leucyl-N-[1-[2-[5-phenyl]-1,3,4-oxadiazolyl]carbonyl]-4-(guanidino)-butyl-L-leucyl amide;

Acetyl-L-leucyl-N-[1-[3-[5-methyl]-1,2,4-oxadiazolyl]carbonyl]-ethyl-L-leucyl amide;

Acetyl-L-leucyl-N-[1-[3-[5-methyl]-1,2,4-oxadiazolyl]carbonyl]-4-(guanidino)-butyl-L-leucyl amide;

Acetyl-L-tyrosinyl-L-valyl-N-[1-[2-[(5-phenyl)-1,3,4-oxadiazolyl]carbonyl]-2-carboxy-ethyl]-L-alanine amide;

Acetyl-L-Aspartyl-Valyl-N-[1-[2-[(5-phenyl)-1,3,4-oxadiazolyl]carbonyl]-2-(carboxy)-ethyl]-L-glutamyl amide;

(Benzyloxycarbonyl)-L-valyl-N-[1-(2-[5-(3-methylbenzyl)-1,3,4-oxadiazolyl]carbonyl)-2-(S)-methylpropyl]-L-prolinamide;

(t-butoxysuccinyl)-L-valyl-N-[1-[3-[5-(3-trifluoromethylbenzyl)-1,2,4-oxadiazolyl]carbonyl]-2-benzylidone]-L-prolinamide; and Carboxysuccinyl-L-valyl-N-[1-[3-[5-(3-trifluoromethylbenzyl)- 1,2,4-oxadiazolyl]carbonyl]-2-benzylidone]-L-prolinamide.

The present invention also provides a method of inhibiting cancer cell growth or tumor progression or tumor metastasis or invasion, by inhibiting the enzymatic activity of cysteine proteases associated with such growth or progression, such as cathepsin B or cathepsin L.

Further provided is a method of inhibiting microbial cell or viral growth or reproduction by inhibiting the enzymatic activity of cysteine proteases associated with such growth or reproduction. Suitable pathogenic targets include, by example only, hepatitis A virus 3C proteinase, hepatitis C virus endopeptidase 2, picomain 3C rhinovirus protease, encephalomyelitis virus endopeptidase 2 and picomain 2A protease.

The present invention also provides a method of treating the symptoms associated with allergic responses by inhibiting the enzymatic activity of cysteine proteases associated with certain allergens, such as, for example Der p I.

The invention provides a method of treating the symptoms associated with neurodegenerative disorders, such as Alzheimer's disease, Parkinson's disease, multiple sclerosis. The invention further provides a method of treating the symptoms associated with stroke.

Further provided is a method of treating the symptoms associated with inflammatory and degenerative diseases, such as arthridities, including rheumatoid arthritis or osteoarthrtis, or periodontal disease.

As used herein, the term "cysteine protease binding moiety" means a chemical group capable of binding to the substrate binding site of a cysteine protease, typically defined in the literature as the $S_1$–$S_n$ site. The term includes both peptides and peptide mimetics. Preferably, the binding moiety is selected such that when linked to the keto-heterocycle, the moiety provides the resulting compound with inhibitory activity against the target cysteine protease of less than 100 μM ($K_i$ value); and more preferably of less than 10 μM.

As used herein, the term "optionally substituted" means, when substituted, mono to fully substituted.

As used herein, the term "independently" means that the substituents may be the same or different.

As used herein, the term "alkyl" means $C_1$–$C_{15}$, however, preferably $C_1$–$C_7$.

As used herein, the term "alkenyl" means $C_1$–$C_{15}$, however, preferably $C_1$–$C_7$.

As used herein, the term "alkynyl" means $C_1$–$C_{15}$, however, preferably $C_1$–$C_7$.

It will be understood that alkyl, alkenyl and alkynyl groups, whether substituted or unsubstituted, may be linear or branched.

As used herein, the term "aryl," unless otherwise stated, means aryl groups preferably comprising 5 to 12 carbons, and more preferably 5 to 6 carbons. Unless otherwise indicated, the term aryl includes mono-and bi-cyclic, as well as fused ring systems. As used herein, the term "arylalkyl" includes mono-substituted alkyl groups (e.g., benzyl), as well as di-substituted alkyl groups such as -alkyl(phenyl)$_2$ (e.g., —CH(phenyl)$_2$). As used herein, where the term "arylalkyl" or "arylalkenyl" is defined by the general formula ($C_x$–$C_y$)arylalkyl or ($C_x$–$C_y$)arylalkenyl, x and y refer to the number of carbons making up the aryl group. The alkyl group is as defined above. As used here, the term "arylalkenyl" includes aryl compounds having an alkenyl chain comprising 1–3 or more double bonds. Exemplary arylalkenyl groups include =CH—CH$_2$-aryl and —CH=CH-aryl, where aryl is preferably phenyl.

As used herein, the term "arginine mimetic" means an amino acid residue with a side chain substituent of the formula —R'—C(=$^+$NH$_2$)NH$_2$; —R'—NHC(=$^+$NR")NR°; or —R'—NR"R° where R' is cycloalkyl, aryl or arylalkyl optionally substituted with one or more heteroatoms selected from N, S or O; and R" and R° are alkyl or cycloalkyl.

As used herein, the term "Cbz" means benzyloxycarbonyl; and the term "Mu" means morpholino.

Pharmaceutically acceptable salts of the compounds described above are within the scope of the invention.

DETAILED DESCRIPTION OF THE INVENTION

Figure 1:
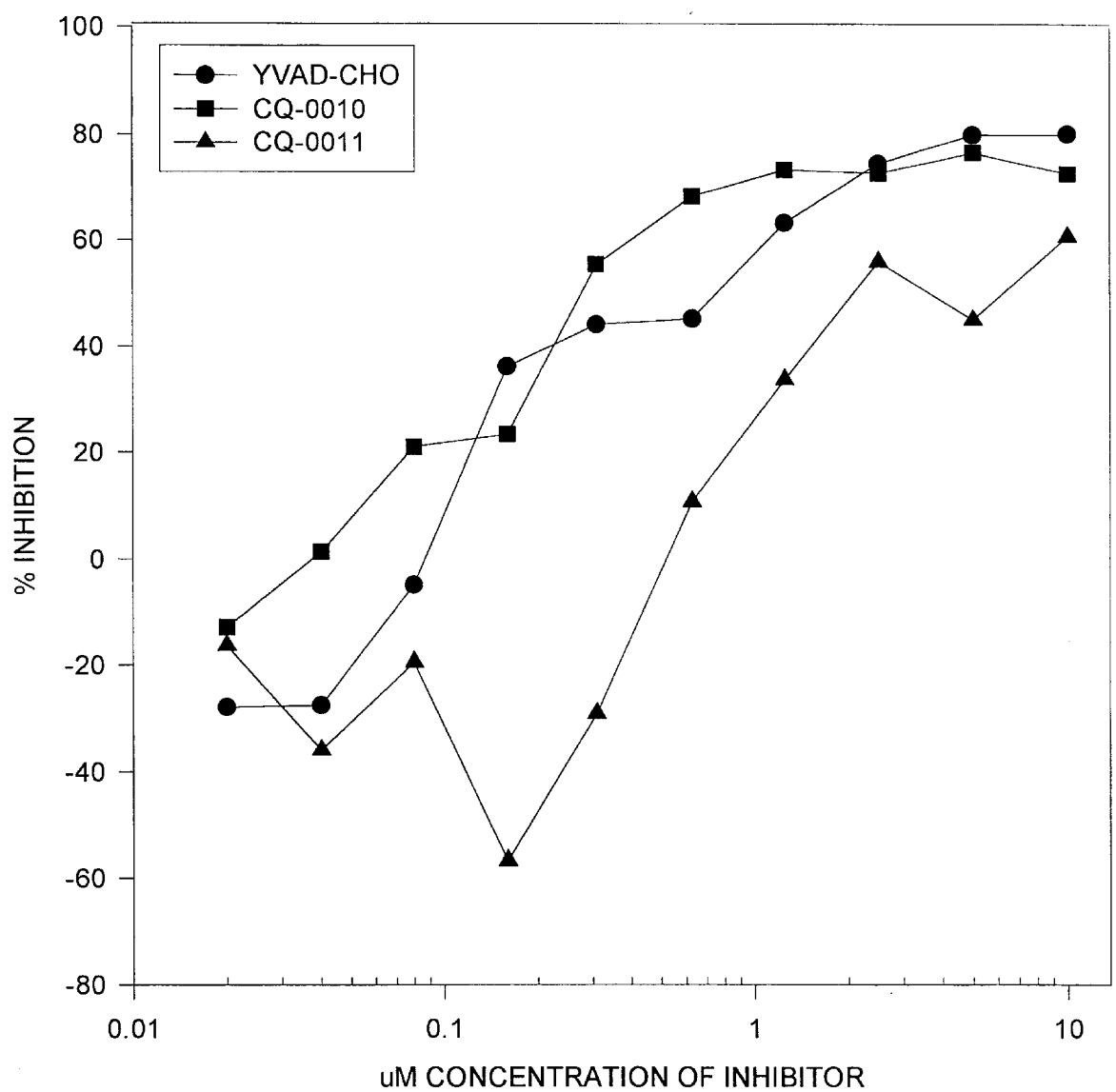
FIG. 1 shows the inhibition of the production of mature IL-1β in THP-1 cell line by certain compounds of the present invention.

The present invention provides compounds which are useful as cysteine protease inhibitors. These compounds are characterized by their relatively low molecular weight, reversible inhibition, high potency and selectivity with respect to various types of cysteine proteases. The compounds can be implemented to prevent, alleviate and/or otherwise treat diseases which are mediated by the effects associated with the presence of cysteine proteases. Their usage is of particluar importance as they relate to various human treatments in vivo and as well as diagnostic tools in vitro.

Peptidyl inhibitors of serine proteases comprising serine protease binding moieties and certain keto-heterocycles have been previously described (see WO 96/16080). It has been surprisingly found that compounds comprising cysteine protease binding moieties and these keto-heterocycles are highly potent and specific inhibitors of a wide variety of cysteine proteases as well. The inhibiting activity can be directed against any cysteine protease by identifying the binding moiety specific for that protease. The characteristics for the $P_1$ . . . $P_n$ residues (using substrate nomenclature by Schechter and Berger (*Biochem. Biophys. Res. Commun.* 27: 157 (1967); *Biochem. Biophys. Res. Commun.* 32: 898 (1968)), which define the minimum recognition sequence of enzymes for small synthetic peptide substrates or inhibitors are known for many enzymes or can be determined by measuring rates of hydrolysis of various substrates. Some examples are listed in Table 1.

TABLE 1

Cysteine proteases and exemplary recognition elements.

| Cysteine Protease | P1 | P2 | Other | Reference |
|---|---|---|---|---|
| Calpain I and II | large hydrophobic e.g. Nva, Phe, Abu | Leu, bulky aliphatic, hPhe | | 18 |
| Calpain I | Arg or Arg- | t-butyl-Gly, Leu, | | 38 |

TABLE 1-continued

Cysteine proteases and exemplary recognition elements.

| Cysteine Protease | P1 | P2 | Other | Reference |
|---|---|---|---|---|
| | mimetic, Lys, Tyr, Val, Nle, Tyr(O-Bzl), Leu, Abu, Phe | Val, hPhe | | |
| Papain | hPhe, Arg or its mimetics, Agly, Aala | bulky, non-polar, Phe | | 22 |
| Cathepsins Cysteine (in general) | bulky hydrophobic residues like hPhe, Phe, Met, Abu, Nva, or Arg and its mimetics | Val, Leu | | 18, 21, 22, 25 |
| Cathepsin B | hPhe, Phe, Tyr, Ser(OBzl), Thr(OBzl), Cys(SBzl), Arg or its mimetics, Gly | Phe, Arg or its mimetics, Leu, Tyr, Np2, Lys, Ornithine | P3 - large hydrophobic aromatic, Ile | 42 |
| Cathepsin S | Val, Nle, hPhe, Phe | Leu, Phe, Val | | 42, 43 |
| Cathepsin L | hPhe, Lys | Phe, Leu | | 42 |
| Cathepsin K | Arg or its mimetics, hPhe, Leu | Pro, Leu, Phe, Val | P3 - Leu | 44 |
| Cathepsin H | | Arg or its mimetics, hPhe | | |
| Caspases | Asp | | P4 - determines the specificity within the caspase family | 22, 40 |
| Interleukin-1β converting enzyme | Asp | | P3 - Val, Glu or ester thereof P4 - Tyr; Leu | 22, 36, 41, 45, 48 |
| Caspase 3 (YAMA) | Asp | | P4 - Lys | 40, 41 |
| Caspase 8 (FLICE) | Asp | Val | P3 - Glu P4 - Asp | 40, 41 |
| Picornain 3C | Gln or its derivatives (e.g. dimethylGln, Azogln), Glu and its derivatives | Phe, Gly | P3 - Ile P4 - small hydrophobic residues | 9 |
| Human Rhinovirus 3C protease | Gln or its derivatives (e.g. dimethylGln, Azogln), Glu and its derivatives | Phe | P3 - Leu | 8 |
| Hepatitis A Virus 3C proteinase | Gln or its derivatives (e.g. dimethylGln, Azogln), Glu and its derivatives | Ala, Val, Leu, Nle, Phe | P3 - Arg or its mimetics, Ala P4 - hydrophobic residues | 14 |
| Human Corona Virus protease | Arg or its mimetics | Val, Leu, Nle | P3 - Asp or its esters | 1 |
| Hepatitis C Virus endopeptidase 2 | Leu | Leu | P3 - Arg or its mimetics | 8 |
| Ad2 23K protease | Gly | Gly | P3 - Ala, P4 - Leu | 8 |
| Trypanosoma, Leishmania protease | Arg or its mimetics, Lys, Tyr, Ala | Phe, Leu, Val | P3 - Pro, Val, Leu | 23 |
| Picornain 2A | Gln or its derivatives (e.g. dimethylGln, Azogln), Glu and its derivatives, Tyr, Val, Ala | Thr, Gly, Pro | P3 - Ala | 9, 46 |
| Gingipain K | Lys, Orn | | | 30, 47 |
| Gingipain R | Arg or its mimetics | Pro, Leu | P3 - Leu | 30 |
| Malarial hemoglobinase | hPhe, Arg or its mimetics, Lys, Val, Ser(OBzl), ImNva, Tyr | large hydrophobic residues, e.g. Phe, Leu | P3 - Val | 23a |

Nva = norvaline; Abu = α-aminobutyric acid; Agly = azaglycyl; Aala = azaalanyl; Np2 = 2-naphthylalanine; Nle = norleucine; Eps = epoxysuccinyl In addition to altering the binding moiety Z, the substituent on the heterocycle (i.e., $R_1$) can be varied to further increase the specificity of these compounds toward the desired cysteine protease.

By way of example, the compound CM-0019 comprises the binding moiety specific for papain and a substituted 1,3,4-oxadiazole:

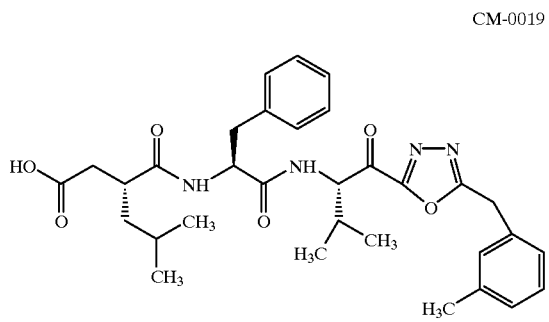

CM-0019

By way of flirther example, the compounds CQ-0010 and CQ-0011 inhibit caspases. Compounds CQ-0002 and CQ-0008 are analogs of leupeptin, the structure of which is provided below for comparison.

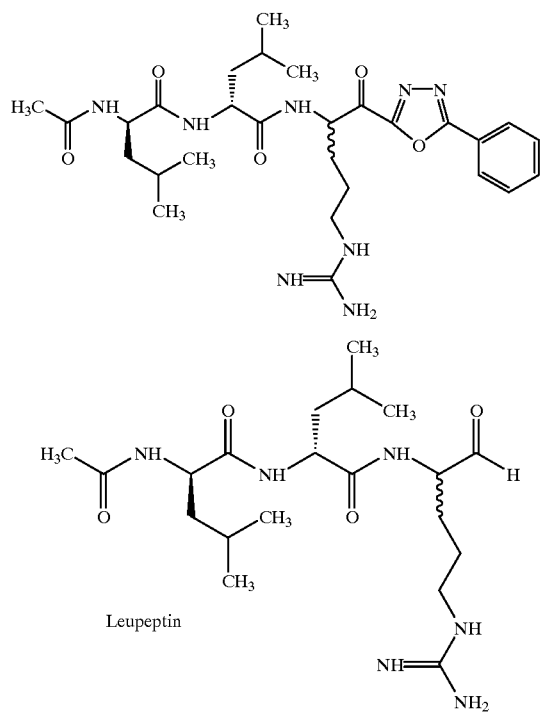

Compounds CQ-0004, 0008, 0010 and 0011 are represented below:

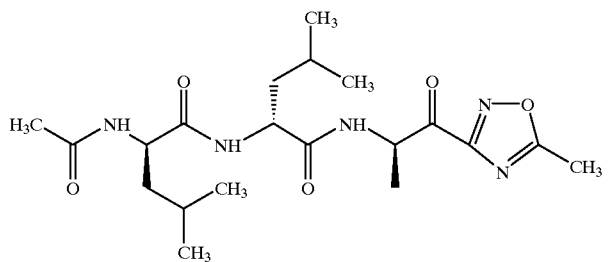

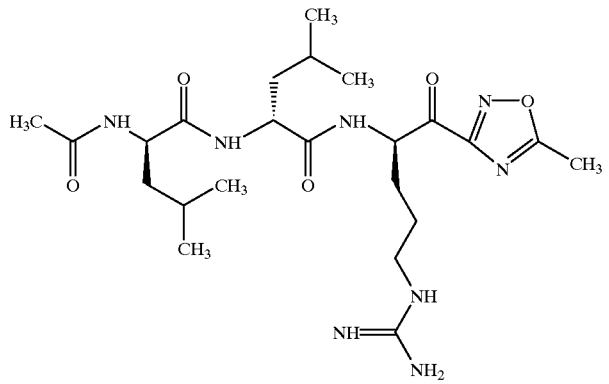

CQ-0010
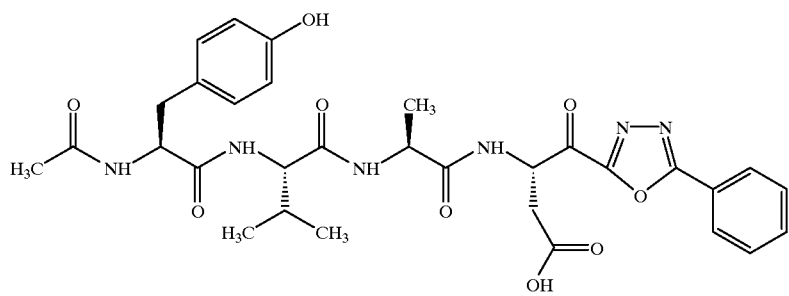
CQ-0011
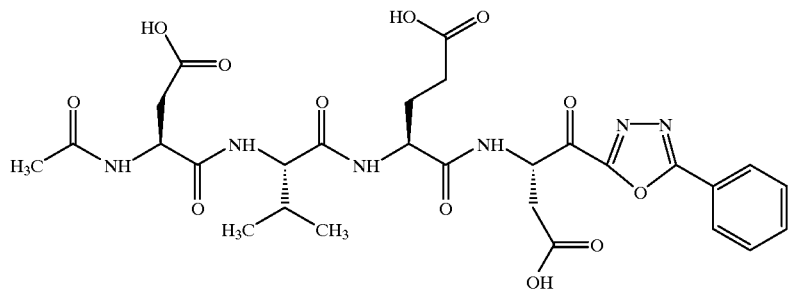
Other specific inhibitors include compounds CE-2072, CE-2060 and CE-2061, which have shown inhibitory activity against picornain 2A protease (100% inhibition at 100 μM):
CE-2072
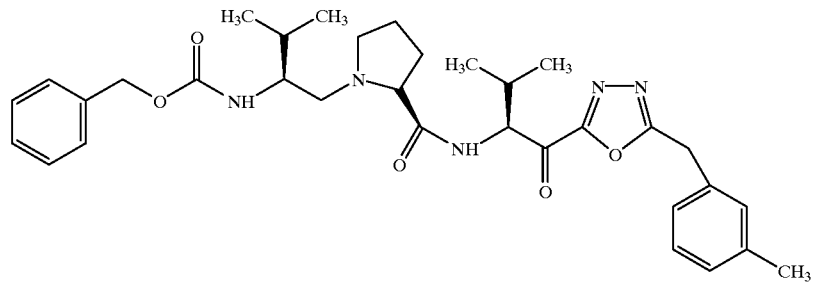
CE-2060
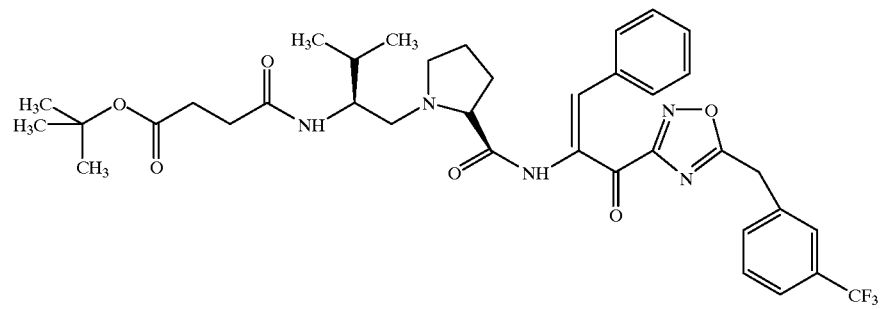

CE-2061

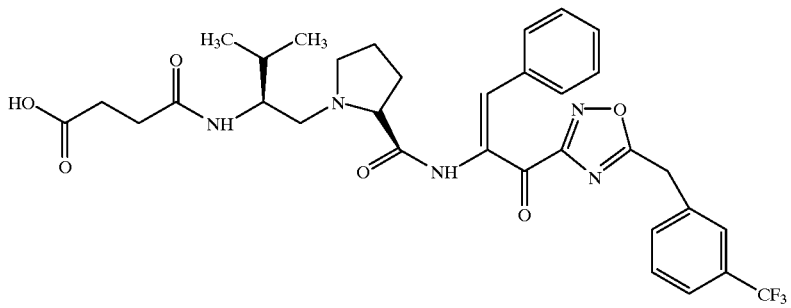

The compounds of the present invention, salts thereof, and their intermediates can be prepared or manufactured as described herein or by various methods known in the chemnical art, as well as by extension and modification of methods previously described (see WO 96/16080, incorporated herein by reference).

An alternative method has been used where suitably protected peptides are converted by the action of an activating coupling reagent such as BOP-Cl or HBTU to a Weinreb amide. The Weinreb arnide is then reacted with a 5-substituted 2-lithio-1,3,4-oxadiazole at appropriate temperatures ranging from −78° C. to ~25° C. in a suitable solvent such as THF or ether to provide the desired keto-oxadiazoles in a single step. Protecting groups, if present, are then removed to provide the enzyme inhibitors in an efficient and convergent manner. A number of efficient methods to synthesize 5-substituted 1,3,4-oxadiazoles are known in the art. Conveniently, these compounds can be synthesized in a single step by refluxing hydrazides of common carboxylic acids with excess ethyl orthoformate at high temperature. The excess orthoformate is hydrolyzed in the workup and the 5-substituted 1,3,4-oxadiazoles are often obtained in essentially pure form without flrther purification necessary. This entire method of synthesis is illustrated in general form in scheme 1 below. Instances where $R_2$ correlates to the amino acid side chains of aspartic acid, arginine, and alanine are provided in the Examples.

pound with the targeted protease, either in an in vivo or an in vitro environment. As used herein, the term "contacting" means directly or indirectly causing the inhibitor and the protease to come into physical association with each other. Contacting thus includes physical acts such as placing the inhibitor and protease together in a container, or administering the inhibitors to a patient. Thus, for example, administering a compound of the invention to a human patient evidencing a disease or disorder associated with abnormal and/or aberrant activity of such proteases in a method for inhibiting the enzymatic activity of such proteases which are associated with disease or disorder, falls within the scope of the definition of the term "contacting."

Pharmaceutically acceptable salts of the cysteine protease inhibitors also fall within the scope of the compounds as disclosed herein. The term "pharmaceutically acceptable salts" as used herein includes organic and inorganic acid addition salts such as chloride, acetate, maleate, fumarate, tartrate and citrate. Examples of pharmaceutically acceptable metal salts are alkali metal salts such as sodium salt or potassium salt, alkaline earth metal salts such as magnesium salt and calcium salt, aluminum salt and zinc salt. Examples of pharmaceutically acceptable ammonium salts are ammonium salt, trishydroxymethylaminomethane and tetramethylammonium salt. Examples of pharmaceutically acceptable amino acid addition salts are salts with lysine, glycine and phenylalanine.

Scheme 1.

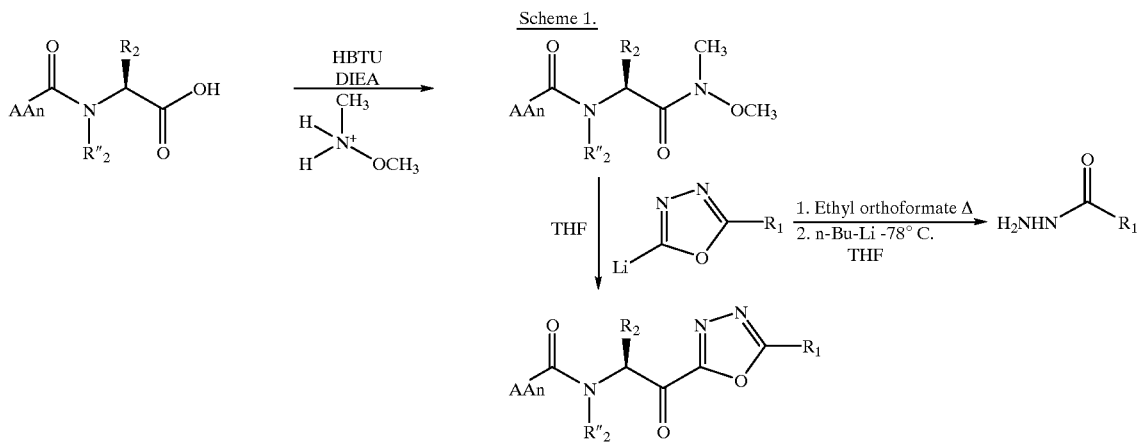

where $AA_n$ means $AA_2 \ldots AA_5$.

The compounds described herein are useful in inhibiting the activity of cysteine proteases, by contacting the com- Cysteine proteases which may be inhibited by the compounds described herein include mammalian, bacterial, parasite, viral, fingal, insect and plant cysteine proteases.

Cysteine proteases include papain, actinidain, aleurain (barley), allergen (Dermatophagoides), allergen (Euroglyphus), ananain (Ananas comosus), asclepain (Asepias syriaca), bleomycin hydrolase, calotropin (Calotropis), caricain, clostripain, cathepsin B, cathepsin H, cathepsin L, cathepsin S, cathepsin O, cathepsin K, cathepsin T, chymopain, cysteine aminopeptidase (Lactococcus), cysteine endopeptidases 2 and 3 (barley), cysteine endopeptidases (Brassica napus), cysteine endopeptidase (Caenorhabditis), cysteine endopeptidases 1 and 2 (Dictyostelium), cysteine endopeptidase (Entamoeba), cysteine endopeptidases 1 and 2 (Haemonchus), cysteine endopeptidase (Hemerocallis), cysteine endopeptidases 1, 2 and 3 (Homarus), cysteine endopeptidase (Leishmania), cysteine endopeptidase (mung bean), cysteine endopeptidase (Ostertagia), cysteine endopeptidase (pea), cysteine endopeptidase (Plasmodium), cysteine protease tpr (Porphyromonas), cysteine endopeptidase (Tetrahymena), cysteine endopeptidase (Theileria), cysteine endopeptidase (tobacco), cysteine endopeptidase (Trypanosoma), dipeptidyl peptidase I, endopeptidase (baculovirus of Autographa), endopeptidase EP-Cl (Phaseolus vulgaris), glycyl endopeptidase, oryzain (includes α, β and γ) (rice), bromelain (including stem-and fruit bromelain), ficin, thaumatopain (Thaumatococcus); gingipain R and gingipain K; calpains, including calpain (Schistosoma), calpain I, calpain II, calpain p94, calcium-binding protein PMP41, sol gene product (Drosophila); streptopain and cysteine endopeptidase (Porphyromonas); picomain 2A, picornain 3C, apothovirus endopeptidase, cardiovirus endopeptidase, comovirus endopeptidase, nepovirus endopeptidase; tobacco etch virus NIa endopeptidase, hepatitis C virus endopeptidase 2, adenovirus endopeptidase; tobacco etch virus HC-proteinase; chestnut blight virus p29 endopeptidase; chestnut blight virus p48 endopeptidase; sindbis virus nsP2 endopeptidase; mouse hepatitis virus endopeptidase, avian infectious bronchitis virus endopeptidase; a-clostripain; ubiquitin carboxyl-terminal hydrolase; deubiquinating enzyme (DOA4 protein), ubiquitin-specific processing peptidase 1, ubiquitin-specific processing peptidase 2, ubiquitin-specific processing peptidase 3, tre oncogene protein (human), unp protein (mouse); hemoglobinase (Schistosoma), legumain (jack bean); interleukin converting enzyme and caspases, such as caspase 2 (ICH-1), caspase 3 (CPP32, YAMA), caspase 4 (ICErel-II), caspase 5 (ICErel-III), caspase 6 (Mch2), caspase 7 (Mch3), caspase 8 (FLICE, Mch5), caspase 9 (Mch6, ICE-LAP6), caspase 10 (Mch4); pyroglutamyl-peptidase I; microsomal ER60 protein endopeptidase; prepilin leader peptidase; PRRS arteritis virus PCP α-endopeptidase, equine arteritis virus Nsp2 endopeptidase; foot and mouth disease virus L proteinase; hepatitis A viral protease; human corona virus protease; encephalomyelitis virus endopeptidase; malarial hemoglobinase; drosophila hedgehog virus gene product; dipeptidyl peptidase I (cathepsin C); Der pI (dust mite); γ-glutamyl hydrolase; Actinide (Actinidia); yeast cysteine proteinase E, yeast proteinase D, yeast proteinase F; cancer procoagulant; and histolysin. Enzyme inhibitors for cysteine proteases may be useful as potential therapeutic drugs for humans or animals, as diagnostic or research tools, as antibacterial agents, herbicides, fungicides or pesticides. Potential indications for cysteine protease inhibitors described herein, used in prophylaxis, cure or therapy, include:

Cardiovascular disorders—ischemia reperfusion injury from transplantation and/or vascular surgery, angiogenesis, neovascularization, acute cardiac allograft dysfunction, ischemic cardiac damage, chemotherapy-induced myocardial suppression;

Inflammatory disorders - rheumatoid arthritis and other inflammatory arthritidies, inflammatory bowel disease, inflammatory peritonitis, sepsis, systemic inflammatory response syndrome, multiple organ failure;

Musculo-skeletal disorders—osteoarthritis, osteoporosis, muscular dystrophy, myositis;

Neurological disorders—multiple sclerosis, stroke, Alzheimer's disease, prion-associated disorders, ataxia telangiectasia, central nervous system injury;

Pulmonary disorders—asthma, COPD, adult respiratory distress syndrome, Wegeneres granulomatosis, emphysema;

Allergic, immunologic and autoimmune disorders— house dust mite allergy, transplant rejection, graft verses host disease, Type 1 diabetes mellitus, autoimmune thyroiditis, psoriasis, antibody-mediated autoimmune diseases, lupus erythematosus, Sjogren's syndrome, autoimmune encephalomyelitis;

Solid tumors, lymphomas, leukemias and other malignancies and related disorders—acute and chronic myelogenous leukemia, neuronal cancer, cancer invasion and metastasis, tumor angiogenesis, B and T cell lymphomas, acute and chronic lymphocytic leukemia, resistance to chemotherapy, cancer associated coagulopathies (including deep venous thrombosis, coronary artery disorder, pulmonary embolism, disseminated intravascular coagulation), Hodgkins disease, carcinomas of the colon, liver, lung, breast, kidney, stomach, pancreas, esophagus, oral pharynx, intestine, thyroid, prostate, bladder, brain; osteo-sarcoma, chondro-sarcoma and liposarcoma; neuroblastoma; melanoma; and carcinomas derived from amnion and/or chorion);

Infectious diseases and associated syndromes—septic shock (including Gram-negative sepsis), HIVinfection and AIDS, genital herpes, zoster, chickenpox, EBV infections and encephalitis, CMV-choreoretinitis or encephalitis, cytomegalovirus infections in neonates (including related pneumonitis), opportunistic infections in immunocompromised individuals (including AIDS and transplant patients), dysentery, hepatitis C, hepatitis A, keratoconjuctovitis, bronchopneumonia (including pneumonia in immunocompromised individuals), gastroenteritis, malaria, rhinovirus, polio, enterovirus infections, common cold, aseptic meningitis, foot and mouth disease, Klebsiella pneumonia infection, escherichia coli or staphylococcus epidermidis, leprosy bacteremia, otitis media, lambliasis, non-atopic sinusitis, fulininant hepatitis;

Kidney disorders—polycystic kidney disease, glomerulonephritis;

Other miscellaneous disorders—periodontal disease, alcohol hepatitis, prostate hypertrophy, trauma, cutaneous mastocytosis, radiation- and HIV-induced diarrhea, cachexia (including acompanying cancer and malnutrition).

Examples of cysteine proteases and associated disease are described in Table 2.

TABLE 2

| Cysteine Protease | Disease State | References |
|---|---|---|
| Interleukin 1β converting enzyme (ICE, Caspase 1) | Stroke, traumatic brain injury, organ transplant rejection and septic shock. Inflammatory disorders including the arthritides, such as rheumatoid arthritis and osteoarthritis, inflammatory bowel disease, ulcerative colitis, pancreatitis, and inflammatory peritonitis, asthma. | Patel, et al., FASEB, 10:587–597 (1996);. Barr et al., Bio/Technology, 12:487–493 (1994); Epstein, New Eng. J. Med., 328:106–113 (1993). |
| YAMA (Apopain, CPP32, Caspase 3), FLICE (Mch5, Caspase 8), and other caspases | Diseases in which disregulated apoptosis plays a role in pathology: Solid tumors, B cell lymphoma, chronic lymphocytic leukemia, prostate hypertrophy, preneoplastic liver foci, resistance to chemotherapy, stroke, Alzheimer's disease, Parkinson's disease, multiple sclerosis, prion-associated disorders, ataxia telangiectasia, ischemic cardiac damage, chemotherapy-induced myocardial suppression, AIDS, type I diabetes, lupus erythematosus, Sjogren's syndrome, glomerulonephritis, dysentery, inflammatory bowel disease, radiation- and HIV induced diarrhea, polycystic kidney disease, anemia or erythropoiesis. | Barr et al., Bio/Technology, 12:487–493 (1994) |
| Malarial Hemoglobinase | Malaria | Rockett, et al., FEB, 259:257–259 (1990) |
| Der p1 | Asthma, house dust mite allergy | Kalsheker, et al., Biochem. Biophys. Research Comm., 221:59–61 (1996) |
| Gingipain K and Gingipain R | Adult Periodontitis | Wingrove, et al., J. Biol. Chem., 267:18902–18907 (1992); DiScipio et al., Immun., 87:660–667 (1996) |
| Cathepsin B, Cathepsin L, Cathepsin S, Cathepsin O and Cathepsin K | Osteoarthritis, osteoporosis, rheumatoid arthritis, Alzheimer's disease, cancer invasion and Metastasis, Parkinson's disease, leukemia, lymphoma, hodgkin's disease, tumors, including those of the bladder, brain, lung, pancreas, prostate, stomach and thyroid | Velasco, et al., J. Biol. Chem., 269:27136–27142 (1994); Takeda et al., FEBS Letters, 359:78–80 (1995); Elliott et al., Persp. in Drug Disc. and Des., 6:12–32 (1996) |
| Cancer Procoagulant | Cancer (including carcinomas of the liver, lung, breast, kidney, colon, kidney; osteo-, chondro-, and liposarcoma; neuroblastoma; melanoma; nonlympocytic leukemia; lymphocytic leukemia) | Alessio et al., Eur. J. Haematology, 45:78–81 (1990); Gordon, Seminars in Thrombosis and Hemostasis, 18:424–433 (1992) |
| Calpain I and II | Osteoporosis, stroke, CNS injury, Alzheimer's disease Additionally, diseases involving dysregulated apoptosis as listed for caspase above. | Karlsson, et al., Neurobiology of Aging, 16:901–906 (1995); Squier, et al., J. Cell. Physiol., 159:229–237 (1994). |
| Calpain p94 | Muscular dystrophy | Calpain p94 and limb-girdle muscular dystrophy, ICOP Letters 1996. |
| Hepatitis C Virus Endopeptidase 2 and Hepatitis C Virus NS3 Endopeptidase | Hepatitis C | Grakoui, et al., Proc. Nat. Acad. Sciences, 90:10583–10587 (1993) |
| Picornain 2A and Picornain 3C Proteases | Rhinovirus, polio, enterovirus infection, common cold, aseptic meningitis, polio | Palmenberg, J. Cell. Biochem. 33:191–198 (1987); Cordingley, et al., J. Virology, 5037–5045 (Dec 1989) |
| Hepatitis A Viral Protease | Hepatitis A | Krausslich, et al., Annu. Rev. Biochem., 57:701–754 (1988). |

TABLE 2-continued

| Cysteine Protease | Disease State | References |
| --- | --- | --- |
| Foot and Mouth Disease Virus L Protease | Foot and mouth disease (Cattle) | Roberts et al., Virology 213:140–146 (1995) |

Although the compounds described herein and/or their salts may be administered as the pure chemicals, it is preferable to present the active ingredient as a pharmaceutical composition. The invention thus further provides the use of a pharmaceutical composition comprising one or more compounds and/or a pharmaceutically acceptable salt thereof, together with one or more pharmaceutically acceptable carriers thereof and, optionally, other therapeutic and or prophylactic ingredients. The carrier(s) must be 'acceptable' in the sense of being compatible with the other ingredients of the composition and not deleterious to the recipient thereof.

Pharmaceutical compositions include those suitable for oral, topical or parenteral (including intramuscular, subcutaneous and intravenous) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration may be presented as discrete unit dosage forms such as hard or soft gelatin capsules, capsules, cachets or tablets each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art., e.g., with enteric coatings.

Oral liquid preparations may be in the form of, for example, aqueous or oily suspension, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservative.

The compounds may also be formulated for parenteral administration (e.g., by injection, for example, bolus injection or continuous infusion) and may be presented in unit dose form in ampules, pre-filled syringes, small bolus infusion containers or in multi-dose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in Fisher et al. (U.S. Pat. No. 4,788,603) or Bawas et al. (U.S. Pat. No. 4,931,279, 4668,504 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention may also contain other adjuvants such as flavorings, coloring, antimicrobial agents, or preservatives.

The compositions may also be administered via inhalation, using a suitable delivery vehicle.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg/day, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, most preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The inhibitors described herein may be also used for the detection and quantification of the activity of a cysteine protease in a pure sample, mixture or biological fluid or tissue. The activity can be measured with a protease substrate in the absence and presence of a known concentration of the inhibitor. Specific inhibitors can also be used to confirm that the observed activity is due to a particular protease.

The inhibitors described herein may also be used to identify and purify cysteine proteases. The inhibitors can be covalently linked to a solid support, such as an affinity column or beads used in batch methods, and used to purify a protease or enrich a mixture containing the protease. The inhibitor may be linked to the solid support or bead either directly or via a linker of variable length, such that linkage does not interfere with the binding properties (see, e.g., Thornberry, N., *Methods in Enz.*, 244:615–31 (1994))

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The following examples are given to illustrate the invention and are not intended to be inclusive in any manner:

EXAMPLES

Abbreviations used herein are defined as follows: DMF - dimethylformamide; HBTU - 2-(1 H-benzotriazole- 1 -yl)-1,1,3,3-tetramethyluronium hexafluorophosphate; DIEA - diisopropylethylamine; THF - tetrahydrofuiran; $CH_3CN$ -acetonitrile; EDTA-$Na_2$ - ethylenediaminetetraacetic acid disodium salt; Mtr - 4-methoxy-2,3,6-trimethylbenzene sulfonyl;Bop-Cl - bis(2-oxo-3-oxazolidinyl)phosphinic chloride; EtOH -ethylalcohol; EtOAc - ethylacetate; LDA - lithium diisopropylamide; EDCI - 1-(3-dimethylaminopropyl)-3-ethylcarbodiimide hydrochloride; NMM - N-methyl morpholine; HOBT - 1-hydroxybenzotriazole; TFA - trifluoroacetic acid.

EXAMPLE I

Synthesis of [[2-[5-(3-methylbenzyl)-1,3,4-oxadiazolyl]carbonyl]-2-(S)-methylpropyl]-L-phenylalanamide-(3R)-(isobutyl)succinic acid (CM-0019).

The intermediate (benzyloxycarbonyl)-L-valyl-N-[1-(2-[5-(3-methylbenzyl)-1,3,4-oxadiazolyl]hydroxymethyl)-2-(S)-methylpropyl]-L-prolinamide was prepared as follows:

a. 3-(S)-Amino-2-(RS)-hydroxy-4-methyl pentanoic acid.

To a solution containing 3-(S)-[(benzyloxycarbonyl) amino]-2-acetoxy-4-methylpentanenitrile (see example 1 of WO 96/16080) (15.2 g, 50.0 mmol) in 183 mL of dioxane was added 183 mL of concentrated hydrochloric acid and 7.45 niL of anisole. The reaction mixture was heated to reflux overnight. The hydrolysis reaction was allowed to cool to room temperature and then concentrated in vacuo. The resulting aqueous solution was extracted with ether (2X). The aqueous phase was placed on a Dowex 50X8-100 column (H+ form, preeluted with deionized water to pH=7). The column was eluted with 2.0 N ammonium hydroxide and the pure fractions concentrated to afford 5.53 g (75%) of 3-(S)-amino-2-(R, S)-hydroxy-4-methylpentanoic acid as a pale yellow solid. FAB MS [M+H] m/z; Calcd: 148, Found: 148.

b. 3-(S)-[(Benzyloxycarbonyl)amino]-2-(R,S)-hydroxy-4-methyl pentanoic acid.

To a solution under an atmosphere of nitrogen containing 1.0 g (6.8 mmol) of 3-(S)-amino-2-(R,S)-hydroxy-4-methylpentanoic acid in 9.5 mL of 1 N NaOH and 10 mL of dioxane was added 1.43 g (8.4 mmol) of benzyl chloroformate. The pH was maintained above pH 8 with 1 N NaOH as needed. The reaction mixture was allowed to stir at room temperature overnight. The reaction was diluted with water and washed with ether. The aqueous layer was acidified with 1 N HCl to pH=2 and extracted with ether (2X). The combined organic layers were dried over magnesium sulfate, filtered and evaporated in vacuo to afford 1.75 g (92%) of 3-(S)-[(benzyloxycarbonyl)amino]-2-(R,S)-hydroxy-4-methylpentanoic acid as a light yellow viscous oil. FAB MS [M+H] m/z; Calcd: 282, Found: 282.

c. 3-(S)-[(Benzyloxylcarbonyl)amino]-2-(R,S)-acetoxy-4-methyl pentanoic acid.

To a solution of 3-(S)-[benzyloxycarbonyl)amino]-2-(R, S)-hydroxy-4-methylpentanoic acid (1.70 g, 6.04 mmol) and pyridine (4.9 mL) was added acetic anhydride (5.7 mL, 6.17 g, 60.4 mmol) dropwise at room temperature. The reaction was allowed to stir overnight and was diluted with ethyl acetate and washed with water (2X). The organic layer was dried over magnesium sulfate, filtered and evaporated in vacuo to give a thick oil. The residue was purified by column chromatography on silica gel with 15% methanol/dichloromethane to afford 1.56 g (80%) of 3-(S)-[(benzyloxycarbonyl)amino]-2-(R, S)-acetoxy-4-methyl pentanoic acid as a light yellow viscous oil. FAB MS [M+H] m/z; Calcd: 324, Found: 324.

d. 1-[(3-Methylphenylacetyl)-2-(2-(R,S)-acetoxy)-3-(S)-[(benzyloxycarbonyl)amino]-4-methylpentanoyl] hydrazine.

To a solution containing 3-(S)-[(benzyloxycarbonyl) amino]-2-(R,S)-acetoxy-4-methylpentanoic acid (2.3 g, 7.11 mmol) in 40 mL of DMF under a nitrogen atmosphere at 0° C. was added 1.31 g (9.69 mmol) of HOBT and 1.36 g (7.09 mmol) of EDCI. After stirring for 30 minutes, 1.20 g (7.31 mmol) of 3-methylphenyl acetic hydrazide [prepared analogously to the monoacid hydrazides cited by Rabins et. al. (*J. Org. Chem.*, 30:2486 (1965))] and 1.0 mL (9.10 mmol) of NMM were added. The reaction was allowed to warm to room temperature and stir overnight. The reaction was diluted with ethyl acetate and washed with 5% potassium hydrogen sulfate, saturated sodium bicarbonate, brine and water. The organic phase was dried over magnesium sulfate, filtered and evaporated under reduced pressure. The residue was purified by column chromatography on silica gel with 10% methanol/dichloromethane to afford 2.31 g (89.0%) of the title compound as a white solid. FAB MS [M+H] m/z; Calcd: 470, Found: 470.

e. 1-[2-[5-(3-Methylbenzyl)-1,3,4-oxodiazolyl]-1-acetoxy-2-(S)-(benzyloxycarbonyl)amino]-3-methylbutane.

A solution containing 2.31 g (4.92 mmol) of 1-[(3-methylphenylacetyl)-2-(2-(R,S)-acetoxy)-3-(S)-[(benzyloxycarbonyl)amino]-4-methylpentanoyl]hydrazine in 25 mL of pyridine and 1.88 g (9.86 mmol) of toluene sulfonyl chloride was heated at reflux under a nitrogen atmosphere for 72 hours. The solvent was removed under reduced pressure and the residue dissolved in ethyl acetate and washed with water. The organic phase was dried over magnesium sulfate, filtered and evaporated under reduced pressure. The residue was purified by column chromatography on silica gel with 5% ethyl acetate/hexane to afford 1.41 g (63.5%) of the title compound. FAB MS [M+H] m/z; Calcd: 452, Found: 452.

f. 1-[2-[5-(3-Methylbenzyl)-1,3,4-oxadiazolyl)]-2-(S)-(benzyloxycarbonyl)amino]-3-methylbutan-1-ol.

A solution containing 1.80 g (3.99 mmol) of 1-[2-[5-(3-methylbenzyl)-1,3,4-oxadiazolyl)-1-1-acetoxy-2-(S)-(benzyloxycarbonyl)amino]-3-methylbutane and 0.72 g (5.21 mmol) of potassium carbonate in 30 mL of methanol and 8 mL of water was allowed to stir at room temperature for 30 minutes. The solvent was removed under reduced pressure and the residue dissolved in ethyl acetate and washed with water. The organic phase was dried over magnesium sulfate, filtered and evaporated under reduced pressure. The residue was purified by column chromatography on silica gel with 60% ethyl acetate/hexane to afford 1.46 (89.3%) of the title compound. FAB MS [M+H] m/z; Calcd: 410, Found: 410.

g. 1-[2-[5-(3-Methylbenzyl)-1,3,4-oxadiazolylj-2-(S)-Amino-3-methylbutan-1-ol hydrochloride.

To a solution containing 1.31 g (3.20 mmol) of 1-[2-[5-(3-methylbenzyl)-1,3,4-oxadiazolyl]-2-(S)-(benzyloxycarbonyl)amino]-3-methylbutan-1-ol in 25 mL of trifluoroacetic acid under a nitrogen atmosphere at 0° C. was added 0.43 mL (3.94 mmol) of thioanisole. The reaction was allowed to warm to room temperature overnight. The solvent was removed under reduced pressure and the residue dissolved in ether and cooled to −78° C. under a nitrogen atmosphere. To this solution was added 3 mL (3 mmol) of 1 N hydrochloric acid in ether. The resulting white solid was allowed to settle and the ether decanted. Additional ether was added and decanted (3X). The solid was dried under vacuum to afford 0.92 g (92.2%) of the title compound. FAB MS [M+H] m/z; Calcd: 276, Found: 276.

(4S)-4-Benzyl-3-[4'-(methyl)pentanoyl]-2-oxazolidinone a. 4-Methylvaleric acid (6.56 g, 55.6 mmol) was dissolved in dry $CH_2Cl_2$ (40 ml) under $N_2$ and chilled to 4° C. Oxalyl chloride (5.4 mL, 63.5 mmol) was added; followed by 4 drops of dry DMF. Rapid $CO_2$ evolution occured. The reaction mixture was allowed to warm to ambient temperature over 2 h; no more $CO_2$ evolution was apparent. Solvents were stripped by rotary evaporation and the acid chloride was distilled in vacuo. $^1$H-NMR (300 MHz, $CDCl_3$) δ 0.88–0.93 (m, 6H), 1.59–1.64 (m, 3H), 2.90 (t, 2H, J=7.5 Hz).

b. (S)-(−)-4-benzyl-2-oxazolidinone (8.93 g, 50.4 mmol) was dissolved in dry THF under $N_2$ and chilled to −78 ° C. nButyl lithium (1.6 M in hexane, 32 mL, 50.4 mmol) was added dropwise to maintain temperature <−70° C. The mixture was stirred 25 min. at −78° C., then a solution of the acid chloride prepared above in dry THF (30 mL) was added dropwise to maintain temperature <−65° C. The reaction mixture was stirred overnight and allowed to warm to 15° C. The reaction was quenched by careful addition of saturated $NH_4Cl$ (70 mL). THF was removed under reduced pressure and the resultant aqueous slurry was extracted with EtOAc (100 mL). The organic layer was washed with 0.5 N NaOH, $H_2O$, brine. The organic layer was dried over MgSO4, filtered and evaporated in vacuo to return 12.7 g of crude yellow oil. The crude material was purified by silica gel chromatography (10% EtOAc/hexane) and dried in vacuo to return 9.0 g (69% yield) of pale yellow oil. C-18 HPLC RT=16.5 min., 96% pure at 215 nm (10–100% solv. B/25 min; solvent A=0.1% (v/v)TFA/$H_2O$; solvent B=0.1% TFA/acetonitrile; FAB-MS m/z 276(M+H)$^+$; $^1$H-NMR (300 MHz, $CDCl_3$) δ 0.94 (d, 6H, J=6.3 Hz, ε-[($CH_3$)$_2$]), 1.53–1.72 (m, 3H, β $CH_2$,g CH), 2.76 (dd, 1H, J=13.3, 9.6 Hz, oxazolidinone 5-CHH), 2.90–2.97 (m, 2H), 3.29 (dd, 1H, J=13.2, 3.3 Hz, oxazolidinone 5CHH), 4.15–4.20 (m, 2H), 4.64–4.70 (m, 1H, oxazolidinone 4-CH), 7.17–7.39 (m, 5H, Ph-H).

c. (4S)-4-Benzyl-3-(2'R)-2'-[[(tert-butoxycarbonyl)methyl]-4'-(methyl)pentanoyl]-2-oxazolidinone.

Diisopropylamine (5.05 mL, 36 mmol) was diluted with dry THF (20 mL) and chilled to −20° C. under $N_2$. n-Butyl lithium (1.6 M in hexane, 23 mL, 36 mmol) was added dropwise to maintain the temperature <−10° C. The temperature was increased to 4° C. and stirred 30 minutes to generate LDA. The flask was chilled to −78° C. and (4S)-4-Benzyl-3-[4'-(methyl)pentanoyl]-2-oxazolidinone in dry THF (15 mL) was added dropwise to maintain the temperature <−70° C. The reaction was stirred 30 minutes at −78° C. then t-butylbromoacetate (4.9 mL, 33 mmol) in dry THF was added dropwise to maintain the temperature <−65° C. The mixture was stirred and allowed to warm to −10° C. overnight. After 15 hours, the reaction was quenched by careful addition of water followed by evaporation of the THF. Water (100 mL) was added to the slurry and the crude mixtrure was extracted with EtOAc (100 mL). The organic layer was washed with water and brine; then dried over $MgSO_4$, filtered and dried in vacuo to leave 13.3 g crude yellow oil. Silica gel chromatography in 15% EtOAc/hexane returned 7.84 g (61% yield) of a white solid product. C-18 HPLC RT=19.5 min., 99% pure at 215 nm (10–100% solv. B/25 min; solvent A=0.1% (v/v)TFA/$H_2O$; solvent B=0.1% TFA/acetonitrile; FAB-MS m/z 390 (M+H)$^+$, 334 (M-tBu+H)$^+$. $^1$H-NMR (300 MHz, $CDCl_3$) 60.92 (d, 3H, J=6.0 Hz), 0.94 (d, 3H, J=5.8 Hz), 1.28–1.40 (m, 1H, CHMe2), 1.43 (s, 9H$_3$), 2.49 (dd, 1H, J=16.7, 4.6 Hz), 2.72 (dd, 1H, J=10.3, 1.1 Hz), $CO_2C$ ($CH_3$)$_3$), 2.76 (dd, 1H, J=10.3, 2.2 Hz, Ph-CHH), 3.35 (dd, 1H, J=13.5, 3.1 Hz), 4.15–4.18 (m, 2H), 4.21–4.26 (m, 1H), 4.52–4.61 (m, 1H), 7.27–7.34 (m, 5H, Ph-H).

d. (2R)-2-[(tert-Butoxycarbonyl)methyl]-4-(methyl)pentanoic acid (4S)-4-Benzyl-3-(2'R)-2'-[[(tert-butoxycarbonyl)methyl]-4'-(methyl)pentanoyl]-2-oxazolidinone (5.89, 15.1 mmol) was dissolved in dry THF(100 mL) and water (25 mL) was added. The mixture was chilled to 4° C. under $N_2$. $H_2O_2$ (7.6 mL) was added followed by dropwise addition of LiOH (0.76 g, 18.2 mmol) in $H_2O$ (20 mL) over 20 minutes. The mixture was stirred for 1 hour and allowed to warm to ambient temperature. The mixture was again chilled in an ice bath and quenched by addition of $Na_2SO_3$ (3.1 g) in water (20 mL). THF was removed by rotovap, the remaining aqueous layer was washed with EtOAc (4×70 mL), then acidified to approx. pH 2 with conc. HCl after layering with fresh EtOAc. The mixture was immediately extracted with EtOAc (3×80 mL). The combined EtOAc extracts were dried over $MgSO_4$, filtered, and evaporated to return 3.29 g clear oil (95% crude yield) which showed no traces of starting material by HPLC. This material was used without flirther purification. $^1$H-NMR (300 MHz, $CDCl_3$) δ 0.90 (d, 3H, J=6.4 Hz, $CH_3$), 0.94 (d, 3H, J=6.5 Hz, $CH_3$), 1.20–1.48 (m, 1H, CHMe$_2$), 1.44 (s, 9H, C($CH_3$)$_3$), 1.50–1.72 (m, 2H), 2.37(dd, 1H, J=16.4, 2.4 Hz), 2.59 (dd, 1H, J=16.4, 2.6 Hz), 2.80–2.95 (m, 1H).

e. Tert-butyl(3R)-3-(isobutyl)succinyl-L-phenylalanyl methyl ester.

To a solution of tert-butyl-(3R)-3-(isobutyl)succinate (10.82 g, 47.0 mmols), in 90 ml of dry DMF was added HBTU (17.45 g, 46.0 mmols), followed by DIEA (18.43 g, 142.6 mmols). After stirring for 10 min, L-phenylalanine methyl ester hydrochloride (10.0 g, 46.36 mmols) was added. This was allowed to stir at room temperature overnight. The solvent was removed under reduced pressure and the residue dissolved in 200 ml ethyl acetate. This solution was washed with water, 1 M HCl (2×), saturated NaHCO$_3$ (2×), brine, and the organics were dried with anhydrous MgSO$_4$. The mixture was filtered and the solvent removed under reduced pressure. The residue crystallized to an off-white solid upon sitting overnight, giving 13.3 g (74%) of tert-butyl(3R)-3-(isobutyl)succinyl-L-phenylalanyl methyl ester. C-18 HPLC RT=16.9 min., 98% pure at 215 nm (10 to 100% solvent B/25 min; solvent A=0.1% TFA/H$_2$O; solvent B=0.1% TFA/acetonitrile). FAB-mass spectrur: m/z (M+H)$^+$=392; Theory=392.

$^1$H NMR (CDCl$_3$) δ [0.85 (d, J=7.5 hz); 0.88 (d, J=7.5 hz); 6H]; [1.10–1.23 (m, 1H)]; [1.44 (s, 9H)]; [1.45–1.65 (m, 2H)]; [2.22–2.32 (m, 1H)]; [2.50–2.66 (m, 2H)]; [3.10 (d, J=6 Hz) 2H]; [3.69 (s,3H)]; [4.82–4.92 (m, 1H)]; [6.19 (d, J=9 hz), 1H]; [7.13–7.33 (m, 5H)].

f Tert-butyl(3R)-3-(isobutyl)succinyl-L-phenylalanine.

A solution of tert-butyl(3R)-3-(isobutyl)succinyl-phenylalanyl methyl ester (2.0 g, 5.10 mmols) in 5 ml methanol was cooled to 4° C. in an ice bath. To this solution was added 4 ml of an aqueous solution of lithium hydroxide (333 mg, 7.94 mmols.), and this solution was stirred and allowed to warm to room temperature overnight. The solution was concentrated to an oil under reduced pressure. The residue was dissolved in 100 ml ethyl acetate, washed with 10% citric acid, water, and dried with anhydrous MgSO$_4$. The mixture was filtered and the solvent was removed under reduced pressure, vacuum dried overnight to give 1.8 g (95%)of tert-butyl(3R)-3-(isobutyl)succinyl-L-phenylalanine as a light yellow oil. C-18 HPLC RT=14.7 min., 95% pure at 254 nm (10 to 100% solvent B/25 min; solvent A=0.1% TFA/H$_2$O; solvent B=0.1% TFA/acetonitrile). FAB mass spectrum: M+H=378; theory=378.

$^1$H NMR (CDCl$_3$) δ [0.83 (d,J=6.0 hz); 0.85 (d, J=6.0 hz); 6H]; [1.10–1.25 (m, 1H)]; [1.44 (s, 9H)]; [1.45–1.65 (m, 2H)]; [2.24–2.35 (m, 1H)]; [2.48–2.58 (m, 2H)]; [3.07–3.27 (m,2H)]; [4.79–4.93 (m, 1H)]; [6.36 (d, J=9 Hz), 1H]; [7.20–7.41 (m, 5H)].

g. Tert-butyl(3R)-3-(isobutyl)succinyl-[[2-[5-(3-methylbenzyl)-1,3,4-oxadiazolyl]-(R,S)-hydroxymethyl]-2-(S)-methylpropyl]-L-phenylalaninamide.

To a solution of tert-butyl(3R)-3-(isobutyl)succinyl-phenylalanine (1.8 g, 4.80 mmols) in 40 ml DMF was added HOBT (676 mg, 5.0 mmols). This was cooled in an ice bath to 4° C. EDCI (921 mg, 4.80 mmols) was then added. After stirring for 30 minutes, a solution of [2-[5-(3-methylbenzyl)-1,3,4-oxadiazolyl]-2-(S)-amino-3-methylbutan-1-(R,S)-ol hydrochloride(1.50 g, 4.24 mmols) in 20 ml. DMF was added dropwise, followed by N-methyl morpholine (0.77 g, 7.66 mmols) and the reaction allowed to stir and warm to room temperature overnight. Most of the solvent was removed under reduced pressure and the mixture was diluted with ethyl acetate. It was then washed with saturated NaHCO$_3$, 5% KHSO$_4$, brine, and the organics dried with anhydrous MgSO$_4$. The mixture was filtered and the solvent removed under reduced pressure. The residue was purified by column chromatography (silica gel, ethyl acetate:hexane 50:50 to 65:35) to give 1.30 g, 43% of tert-butyl(3R)-3-(isobutyl)succinyl-[[2-[5-(3- methylbenzyl)-1,3,4-oxidiazolyl]-(R,S)-hydroxymethyl]-2-(S)-methylpropyl]-L-phenylalaninamide as an off-white foamy solid. C-18 HPLC RT=18.3, 18.7 min. diastereomers, 90% pure at 215 nm (10 to 100% solvent B/25 min; solvent A=0.1% TFA/H$_2$O; solvent B=0.1% TFA/acetonitrile). FAB mass spectrum: m/z (M+H)$^+$=635; theory=635.

h. tert-Butyl-(3R)-3-(isobutyl)succinyl-[[2-[5-(3-methylbenzyl)-1,3,4-oxadiazolyl]carbonyl]-2-(S)-methylpropyl]-L-phenylalaninamide.

To a stirred mixture of N-chlorosuccinimide (1.07 g, 8.0 mmols) in 25 ml dry toluene at 4° C. was added 0.84 ml (11.45 mmols) dimethyl sulfide (DMS) under a nitrogen atmosphere. A white precipitate formed after the addition of DMS. After 30 minutes, the resulting suspension was cooled to −25° C. using a carbon tetrachloride and dry ice bath. A solution of tert-butyl(3R)-3-(isobutyl)succinyl-[[2-[5-(3-methylbenzyl)-1,3,4-oxadiazolyl]-(R,S)-hydroxymethyl]-2-(S)-methylpropyl]-L-phenylalaninamide (1.25 g, 1.97 mmols) in 30 ml dry toluene was added dropwise. The resulting mixture was stirred for 1.5 h at −25° C. and 1.19 ml (8.5 mmols) of triethylamine was added. After 15 minutes, the cold bath was removed, and the reaction monitored by TLC; silica gel; ethyl acetate:hexane (30:70). After 1 h, the mixture was diluted with 500 ml ethyl acetate and washed with saturated NaHCO$_3$ brine and the organics dried with anhydrous MgSO$_4$. The mixture was filtered and the solvent removed under reduced pressure. The residue was purified by column chromatography (silica gel, methanol:chloroform, 0.5:99.5 to 2.5:97.5) to give tert-butyl (3R)-3-(isobutyl)succinyl-[[2-[5-(3-methylbenzyl)-1,3,4-oxadiazolyl]carbonyl]-2-(S)-methylpropyl]-L-phenylalaninamide as an off white foamy solid; 1.0 g, (80.2%). C-18 HPLC RT=20.2, 20.7 min. diastereoisomers, 90% pure at 215 nm (10 to 100% solvent B/25 min; solvent A=0.1% TFA/H$_2$O; solvent B=0.1% TFA/acetonitrile). FAB mass-spectrum: m/z (M+H)$^+$=633; theory=633.

i. [[2-[5-(3-methylbenzyl)-1,3,4-oxadiazolyl]carbonyl]-2-(S)-methylpropyl]-L-phenylalaninamide-(3R)-(isobutyl) succinic acid.

To a solution of tert-butyl(3R)-3-(isobutyl)succinyl-[2-[5-(3-methylbenzyl)-1,3,4-oxadiazolyl]carbonyl]-2-(S)-methylpropyl]-L-phenylalaninamide (1.0 g, 1.58 mmol) in 25 ml dichloromethane (DCM) cooled to 4° C. in an ice bath, was added 25 ml trifluoroacetic acid (TFA). This was stirred for 1 h. The solvent and TFA are removed under reduced pressure, followed by coevaporation with DCM (3×). The material was purified via gradient RP-HPLC CH$_3$CN:H$_2$O (25:75 to 100:0 in 60 minutes) to give 292 mg (32%, 0.51 mmols) of which 52 mg was pure as a white solid after lyophilization. C-18 HPLC RT=15.8 mhin., 95% pure at 215 nm (10 to 100% solvent B/25 min; solvent A=0.1% TFA/H$_2$O; solvent B=0.1% TFA/acetonitrile). FAB Mass spectrum: m/z (M+H)$^+$=577; theory=577. $^1$H-NMR(400 MHz, CDCl$_3$)δ 0.76 (d, 3H, J=6.8 Hz), 0.85 (d, 3H, J=6.4 Hz), 0.87 (d, 3H, J=6.4 Hz), 0.93 (d, 3H, J=6.8 Hz), 1.25–1.32 (m, 1H), 1.48–1.61 (m, 2H), 2.28–2.36 (m, 2H), 2.35 (s, 3H), 2.44–2.49 (m, 1H), 2.61–2.69 (m, 2H), 2.95 (dd, 1H, J=13.6, 8.4 Hz), 3.09 (dd, 1H, J=16.6,6.4 Hz),4.24 (s, 2H), 4.67 (dt, 1H, J=8.0, 6.8 Hz), 5.19 (dd, 1H, J=8.4, 6.0 Hz), 6.52 (br. d, 1H, J=8.4 Hz), 6.81 (br. d, 1H, J=7.6 Hz), 6.94–6.99 (m, 1H), 7.10–7.19 (m, 7H). $^{13}$C-NMR(100 MHz, CDCl$_3$) δ 17.26, 19.54, 21.33, 22.13, 22.71, 25.75, 30.84, 31.82, 36.74, 38.16, 40.54, 41.29, 55.16, 61.55, 126.1, 126.8, 128.6, 128.8, 129.0, 129.1, 129.7, 132.5, 136.2, 139.0, 160.2, 167.9, 171.6, 175.0, 175.7, 184.4.

EXAMPLE II

Acetyl-L-leucyl-N-[1-[2-[(5-phenyl)-1,3,4-oxadiazolyl]carbonyl]-4-(guanidino)-butyl]-L-leucyl]amide (CQ-0002).

2-Phenyl-1,3,4-oxadiazole intermediate

Benzoyl hydrazide (200 mg) freshly crystallized from chloroform was suspended in 5 mL of triethyl orthoformate and heated at reflux under nitrogen in a 160° C. oil bath for 3 hours. The mixture was cooled to room temperature, chilled in ice, and treated with 50 mL water and 10 mL 10% $KHSO_4$ solution. The mixture was stirred approximately 2 minutes then 50 mL of EtOAc was added and stirring continued for 10 minutes. The organic layer was separated and the aqueous layer was extracted three times with ethyl acetate. All ethyl acetate layers were combined and were washed with 10% sodium bicarbonate solution and saturated sodium chloride solution. Drying over sodium sulfate, rotary evaporation and further drying under high vacuum provided 204 mg of an analytically pure oil which crystallizes upon standing. Commercially available benzoylhydrazine (Aldrich) in this reaction may be used, but the resulting product often contains a minor impurity which can be removed following the cyclization, by flash chromatography on silica gel eluting with 0–10% acetone in hexane. $^1$H-NMR-CDCl$_3$ 7.49–7.62 (m, 3H), 8.12 (d, J=6, 2H), 8.49 (s, 1H).

A. Acetyl-L-leucyl-L-leucyl-arginine(Mtr) (N-methyl)-(N-Methoxy)-amide:

Acetyl-Leu-Leu-OH (133 mg) and arginine (Mtr) -N-methyl-N-methoxy amide (200 mg) were dissolved in 10 mL of DMF and were treated with 243 uL of DIEA and 212 mg of HBTU. The reaction stirred at room temperature for 15 hours and was worked up according to method A. Drying over Na$_2$SO$_4$, rotary evaporation of the solvent and flash chromatography on silica gel (50% acetone in hexane) provided 270 mg of the title compound as a foam.

B. Acetyl-L-leucyl-N-[1-[2-[(5-phenyl)-1,3,4-oxadiazolyl]carbonyl]-4-[(4-methoxy-2,3,6-trimethyl-benzenesulphonyl)-guanidino]-butyl]-L-leucyl amide:

2-phenyl-1,3,4-oxadiazole (194 mg) in 2 mL of dry THF was chilled to −78° C. n-Butyllithium (1.46 mmole) was added as a 2.5 M solution in hexanes. The reaction stirred 20 minutes at −78° C. and was then placed in a 0° C. cooling bath. Acetyl-Leu-Leu-Arg-(Mtr)-N-(CH$_3$)-OCH$_3$ was then added in 2 mL of dry THF. The reaction was placed in a room temperature water bath and stirred 1 hour, then the solution was. chilled to 0° C., and 20 mL of saturated ammonium chloride solution was added under nitrogen with rapid stirring. After the several minutes of vigourous stirring the solution was extracted with EtOAc. The ethyl acetate solution was washed with saturated sodium chloride solution, dried over sodium sulfate and concentrated to a pale brown oil by rotary evaporation.

C. Acetyl-L-leucyl-N-[1-[2-[(5-phenyl)-1,3,4-oxadiazolyl]carbonyl]-4-(guanidino)-butyl]-L-leucyl amide:

One half of the crude product from step B was dissolved in a pre-formed solution of 2 mL of TFA and 100 uL thioanisole. The reaction stirred under nitrogen for 4 hours. The solvent was removed in vacuo, and the product was precipitated with dry ether. The precipitate was taken up in methanol and concentrated in vacuo, the residue was triturated with dry ether, and dried in vacuo to provide 22 mg of the title compound as a colorless powder. Samples for biological testing were obtained by reverse phase C18 chromatography (5–80% CH$_3$CN, 0.1% TFA, over 40 minutes). MS m/z (M+H)$^+$571 (CQ-0002).

EXAMPLE III

Synthesis of Acetyl-L-leucyl-N-[1-[3-[5-methyl]-1,2,4-oxadiazolyl]carbonyl]-ethyl-L-leucyl amide (CQ-0004)

A. N$^a$-benzyloxycarbonyl-L-alanine (N-methyl-N-methoxy)amide:

Cbz-L-Alanine (1.0 g) was dissolved in 10 mL dry DMF with 1.55 mL of DIEA. HBTU (1.78 g) was added and the reaction Stirred 30 minutes. Dimethyl hydroxyl amine hydrochloride (0.87 g) was added followed by 1.55 mL additional DIEA. The reaction stirred approximately 15 hours at room temperature. Work up according to general method A, drying over anhydrous sodium sulfate, rotary evaporation, and drying under high vacuum produced 0.96 g of a colorless solid.

B. N$^a$-benzyloxycarbonyl-L-alaninal:

A solution of 6 mL of 1 M lithium aluminum hydride in THF was chilled under nitrogen to 0° C. and a solution of compound A (0.68 g ) in 4 mL DMF was added dropwise. After stirring 15 minutes at 0° C. the reaction was carefully quenched with 20 mL of EtOAc and 10 mL of 10% KHSO$_4$ solution. The organic layer was washed with 1 N HCl and 10% NaHCO$_3$ solution. Drying over sodium sulfate, removal of the solvent by rotary evaporation, and drying under high vacuum provided 0.38 g of a colorless oil.

C. 2-(R,S)-3-(S)-[(benzyloxycarbonyl)amino]-2-hydroxy-butanenitrile:

Compound B (1.2 g) triethylamine (0.532 mL) and acetone cyanohydrin (1.56 mL) were dissovled in 10 mL of dry CH$_2$Cl$_2$ and stirred at room temperature for approximately 15 hours. The solvent was removed in vacuo and the residue was taken up in Et$_2$O and washed with saturated sodium chloride solution. Drying over anhydrous sodium sulfate, rotary evaporation, and pumping under high vacuum provided 1.3 g of the cyanohydrin.

D. 2-(R,S)-3-(S)-[(benzyloxycarbonyl)amino]-2-acetoxy-butanenitrile:

Compound C (1.3 g) was dissolved in 2 mL of dry pyridine and was treated with 3.17 mL of acetic anhydride. The reaction stirred at room temperature for 3 hours and was then diluted with ethyl acetate and washed with water. Drying of sodium sulfate, rotary evaporation, and pumping under high vacuum provided 1.34 g of the title compound as an oil.

E. 1-(R,S)-2-(S)-1-[(N-hydroxy)carboximideamido]-1-acetoxy-2-[(benzyloxycarbonyl)-amino]-propane:

Compound D (1.34 g) was dissolved in 21 mL of EtOH and 4.2 mL of water and treated with hydroxylamine hydrochloride (0.422 g) and sodium acetate (0.991 g) and heated at 40 C for 3 hours. The solvent was removed in vacuo and the residue was suspended in EtOAc and washed with water. Drying over sodium sulfate and evaporation of the solvent provided 1.1 g of crude material which was used without further purification.

F. 1-(R,S)-2-(S)-1-[3-[5-(methyl)-1,2,4-oxadiazolyl]-1-acetoxy-2(benzyloxycarbonyl)-amino]]-propane:

Compound E (0.45 g) was suspended in 5 mL toluene and treated with 185 uL of acetic anhydride. The reaction was refluxed for approximately 15 hours, after which the solvent was removed by rotary evaporation and purified by flash chromatography on silica gel eluting with 1:1 hexane:EtOAc to provide 0.36 g of title compound.

G. 1-(R,S)-2-(S)-1-[3-[5-(methyl)]-1,2,4-oxadiazolyl]-2-[(benzyloxycarbonyl)-amino]-propan-1-ol:

Acetate F (180 mg) was dissolved in 3 mL of MeOH and treated with a solution of 90 mg of $K_2CO_3$ in 1 mL of water. After approximately 20 minutes the reaction mixture was diluted with EtOAc and washed with water. Drying over $MgSO_4$, rotary evaporation and drying under high vacuum provided 0.160 g of the title compound.

H. 1-(R,S)-2-(S)-1-[3-[5-(methyl)-1,2,4-oxadiazolyl]-2-amino]-propan-1-ol TFA salt:

Compound G was taken in 2 mL of trifluoroacetic acid and chilled to 0° C. Thioanisole (100 uL) was added and the reaction was allowed to warm to room temperature and stirred approximately 15 additional hours. The solvent was removed in vacuo and traces of remaining TFA were removed by rotary evaporation from dichloromethane and methanol. The crude product was partially purified by elution through a pre-packed C18 mini-column (Waters Sep-Pak) with acetonitrile in water. Lyophilization of appropriate fractions provided the title compound 0.14 g, which was used without further purification.

I. 1-(R,S)-2-(S)-(Benzyloxycarbonyl)-L-leucyl-N-[1-[(3-[5-(methyl)-1,2,4-oxadiazolyl]-hydroxymethyl]-ethyl-]-L-leucine amide:

Compound H (0.14 g) and Acetyl-Leu-Leu-OH were dissolved in DMF (3 mL) and were treated with DIEA (90 uL) and HBTU (234 mg). The reaction was allowed to stir approximately 15 hours at room temperature. The reaction mixture was diluted with EtOAc and washed with water. The water wash was extracted with dichloromethane. All organic layers were combined and concentrated in vacuo. The residue was purified by preparative C18 reverse phase chromatography (5–60% $CH_3CN$, 0.1% TFA) to provide 0.110 g of the title compound upon lyophilization.

J. Acetyl-L-leucyl-N-[1-[3-[5-methyl-1,2,4-oxadiazolyl]carbonyl]-ethyl]-L-leucyl amide:

N-chlorosuccinimide (75.4 mg was suspended in dry toluene and chilled to 0° C. Dimethyl sulfide (60 uL) was added and the suspension stirred 30 minutes at 0° C. and was then chilled to –25° C. Compound I (60 mg) was added in 2 mL dichloromethane and the reaction stirred 2.5 hours at –25° C. Triethyl amine (84 uL) was added and the reaction warmed to room temperature. After stirring 1 hour the reaction mixture was diluted with EtOAc and was washed with water. Drying over anhydrous sodium sulfate and removal of the solvent by rotary evaporation provided 60 mg of crude product. Flash chromatography on silica gel provided 30 mg of the title compound as a colorless solid. MS 424 (M+H). 1H-NMR δ 0.89–0.94 (m, 12 H), 1.50 (d, J=9.6, 3H), 1.53–1.69 (m, 6H), 2.01 (s, 3H), 2.70 (s, 3H), 4.50–4.52 (m, 2H), 5.34–5.39 (m, 1H) 6.23 (d,J=11, 1H), 6.81 (d,J=10.9, 1H), 7.07 (d, J=8.8, 1 H). 13C-NMR δ 12.4, 17.6, 22.1, 22.2,22.8 (2 carbons), 23.1, 24.7,24.8,40.8,41.1, 52.7, 164.1, 170.3, 171.3, 172.3, 178.3, 190.

EXAMPLE IV

Acetyl-L-leucyl-N-[1-[3-[5-methyl-1,2,4-oxadiazolyl]carbonyl]-4-(guanidino)-butyl]-L-leucyl amide (CQ-0007)

A. $N^\alpha$-t-butoxycarbonyl-L-Arg(Mtr)-(N-methyl-N-methoxy)amide: Boc-L-Arg(Mtr)-OH 5.00 g (10.3 mmole) was suspended in dry DMF (10 mL),followed by N,O dimethyl hydroxylamine hydrochloride (1.25 g) and DIEA (5.4 mL). HBTU (4.28 g) was added and the reaction stirred approximately 15 hours at room temperature. The reaction was worked up according to general method A, and the EtOAc solution was dried over $Na_2SO_4$ and concentrated to 5.23 g of a colorless foam.

B. $N^\alpha$-t-butoxycarbonyl-L-(Mtr)-argininal:

Compound A (2.00 g) was dissolved in 20 mL of dry THF and chilled to 0° C. To this solution was added 4.72 mL of a 1 M solution of $LiAlH_4$ in THF, dropwise over 30 minutes at 0° C. The reaction was quenched at 0° C. by the slow addition of 50 mL EtOAc, followed by 15 mL of 10% $KHSO_4$ solution. The mixture was partitioned between 100 mL EtOAc and 50 mL 1 N HCl solution. The organic layer was washed with 1 N HCl solution and saturated sodium chloride solution. The mixture was dried over anhydrous sodium sulfate and concentrated by rotary evaporation. Drying under high vacuum provided 1.74 g of a white solid.

C. 2-(R,S)-3-(S)-[(t-butoxycarbonyl)amino]-6-[(4-methoxy-2,3,6-trimethyl-benzenesulphonyl)-guanidino]-2-hydroxy-hexanenitrile:

Compound B (1.70 g) was dissolved in 25 mL of methanol and was treated with 0.941 g of potassium cyanide. The reaction was allowed to stir at room temperature for approximately 15 hours. The reaction mixture was then partitioned between 150 mnL EtOAc and 25 mnL 1 N HCl. The organic layer was washed with 1 N HCl and dried over anhydrous sodium sulfate solution. Rotary evaporation and further drying under high vacuum provided 1.62 g of the title compound.

D. 2-(R,S)-3-(S)-[(t-butoxycarbonyl)amino]-6-[(4-methoxy-2,3,6-trimethyl-benzenesulphonyl)-guanidino]-2-acetoxy-hexanenitrile:

Compound C (1.62 g) was dissolved in 10 mL of dry pyridine and treated dropwise with 0.62 mL of acetic anhydride. The reaction was allowed to stir at room temperature for 3 hours. The solution was diluted with 100 mL EtOAc and washed three times with equal volumes of 1 N HCl after drying over anhydrous sodium sulfate the solution was concentrated by rotary evaporation to an oil, and purified by flash chromatography on silica gel (50–75% EtOAc in hexanes, step gradient) to provide 0.79 g of the title compound and 0.64 g of mixed fractions containing traces of compound B.

E. 1-(R,S)-2-(S)-1-[(N-hydroxy)carboximideamido]-1-acetoxy-2-[(t-butoxycarbonyl)-amino]-5-[(4-methoxy-2,3,6-trimethyl-benzenesulphonyl)-guanidino]-pentane:

Compound D (0.79 g) was dissolved in 45 mL of EtOAc and 3.9 mL of water and was treated with 0.174 g of sodium acetate and 0.129 g of hydroxylamine hydrochloride. In an analogous fashion the mixed fractions containing compound D (0.64 g) were dissolved in 36.5 mL ethanol and 3.2 mL of water and were treated with 0.141 g of sodium acetate and 0.105 g of hydroxylamine hydrochloride. The reactions were heated at 45° C. for 4 hours with stirring. HPLC analysis showed very similar profiles for both reactions. The reactions were diluted with EtOAc, washed with water and saturated sodium chloride solution and were then dried over anhydrous sodium sulfate and concentrated by rotary evaporation. The combined products were purified by flash chromatography (1–4% MeOH in EtOAc, step gradient) to provide 0.77 g of the title compound.

F. 1-(R,S)-2-(S)-1-[3-[5-(methyl)-1,2,4-oxadiazolyl]-2-amino-5-[(4-methoxy-2,3,6-trimethyl-benzenesulphonyl)-guanidino]-pentan-1-ol trifluoroacetate salt:

Compound E (0.74 g) was dissolved in 6.5 mL of dry chloroform and treated with 0.27 mL of triethyl amine and 0.153 mL of acetic anhydride and allowed to stir 4 hours at room temperature. The reaction was diluted with 50 mL toluene and refluxed for approximately 15 hours in a 120° C. oil bath. The volatile solvents were removed by rotary evaporation and the residue was worked up according to method A. Drying over sodium sulfate, concentration by rotary evaporation, and flash chromatography on silica gel eluting with EtOAc provided 0.34 g of a colorless oil. A portion of this material 0.17 g was dissolved in 4 mL of MeOH and chilled to 0° C. To this solution was added 90 uL of a 4 N solution of $K_2CO_3$. The reaction stirred two hours and was then partitioned between 40 mL of EtOAc and 5 mL water. The organic layer was washed with saturated sodium chloride solution and dried over sodium sulfate. The ethyl acetate was removed by rotary evaporation and traces of ethyl acetate were removed by rotary evaporation from dichloromethane. The resulting residue was diluted in 1.33 mL of dichloromethane and chilled to 0° C. Trifluoroacetic acid (0.57 mL) was added and the reaction stirred 1.5 hour at 0° C. The solvent was rapidly removed in vacuo and the product was dissolved in dichloromethane and concentrated to dryness by rotary evaporation.

G. 1-(R,S)-2-(S)-L-leucyl-N-[1-[(3-[5-(methyl)-1,2,4-oxadiazolyl]-hydroxymethyl]-4-[(4-methoxy-2,3,6-trimethyl-benzenesulphonyl)-guanidino)]-butyl]-L-leucine amide:

Compound F (146 mg) and Acetyl-Leu-Leu-OH (82 mg) were dissolved in 5 mL of dry DMF and treated with 200 uL of DIEA, followed by 30 mg of HBTU. After 5 minutes an additional 100 uL of DIEA was added and the reaction stirred approximately 15 hours at room temperature. The reaction was diluted with EtOAc and washed with saturated $NaHCO_3$ solution and saturated sodium chloride solution. After removal of the solvent by rotary evaporation the product was purified by preparative C18 reverse phase chromatography (5–60% CH3CN, 0.1% TFA) to provide 122 mg of the title compound.

H. Acetyl-L-leucyl-N-[1-[3-[(5-methyl)-1,2,4-oxadiazolyl]carbonyl]-4-[(4-methoxy-2,3,6-trimethyl-benzenesulphonyl)-guanidino]-butyl]-L-leucyl amide:

N-chlorosuccinimide (45 mg) and dimethyl sulfide (61 uL) in 2.5 mL of toluene were chilled to 0° C. with stirring. Stirred at 0° C. for 30 minutes. The mixture was then chilled to ~–25° C. in a dry ice/carbon tetrachloride bath, then compound G (100 mg) was added by dropwise addition in a mixture of 2.5 mL of dichloromethane and 1.5 mL of toluene. The reaction stirred at –25° C. for 3 hours then 100 uL of triethyl amine was added. After 5 minutes the cooling bath was removed, and the reaction stirred 1 hour. The reaction mixture was diluted with EtOAc, and washed with saturated sodium bicarbonate solution and saturated sodium chloride solution. The solution was dried over anhydrous sodium sulfate solution and concentrated to an oil.

I. Acetyl-L-leucyl-N-[1-[3-[(5-methyl)-1,2,4-oxadiazolyl]carbonyl]-4-(guanidino)-butyl-L-leucyl amide:

Compound H was taken up in 1.75 mL of TFA and chilled to 0° C. Thioanisole (90 uL) was added and the reaction stirred 1 hour at 0° C., and 4 hours at room temperature. The volatile solvents were removed by rotary evaporation, and residual TFA was removed by adding dichloromethane and concentrating to dryness on the rotovap. Reversed phase C18 preparative chromatography provided the title compound. FAB MS m/z $(M+H)^+$509 (CQ-0008).

EXAMPLE V

Synthesis of Acetyl-L-tyrosinyl-L-valyl-N-[1-[2-[(5-phenyl)-1,3,4-oxadiazolyl]carbonyl]-2-carboxy-ethyl]-L-alanine amide (CQ-0010)

A. $N^\alpha$-Benzyloxycarbonyl-L-Aspartyl(O-t-butyl) N-methyl-N-methoxy amide: Cbz-L-Aspartic Acid (O-t-butyl) (1.0 g, 2.93 mmole), N,O-dimethyl hydroxyl amine hydrochloride (0.357 g, 3.66 mmole, were suspended in 15 mL of DMF and treated with 1.53 mL (8.79 mmoles) of DIEA under $N_2$ atmosphere. HBTU (1.22 g, 3.22 mmoles) was added and the reaction stirred approximately 15 hours at room temperature. The reaction mixture was worked up according to general extractive work up method A. Drying over $Na_2SO_4$, rotary evaporation of the solvent and ftrther drying under high vacuum provided 1.1 g as a colorless glassy solid.

B. L-Aspartyl-(O-t-butyl) N-methyl-N-methoxy amide:

Compound A (1 g) was dissolved in 20 mL methanol containing 5% (v/v) formic acid. The solution was deoxygenated with nitrogen bubbling then treated with approximately 200 mg of palladium black. The reaction stirred under nitrogen for 3 hours, and was then filtered through celite. The celite was washed well with methanol and the filtrates were combined and concentrated by rotary evaporation. Residual methanol and formic acid were chased off by the addition and rotary evaporation of $CH_2Cl_2$ and 50:50 $CH_2Cl_2$:hexane. Drying under high vacuum provided 790 mg of an oil.

C. Acetyl-L-tyrosinyl-L-Valyl-L-Alanyl-L-Aspartyl-(O-t-butyl) N-methyl-N-methoxy amide:

Compound B (150 mg) and Acetyl-Tyr-Val-Ala-OH (230 mg, prepared using 5 conventional peptide synthesis) were combined and suspended in 10 rnL of DMF. DIEA (305 uL) was added followed by HBTU. Product from normal extractive work up, and the 1 N HCl washes were combined after evaporation and purified by preparative HPLC chromatography (5–60% $CH_3CN$ 0.1% TFA, over 30 minutes) to provide a lyophilized fraction of 85 mg of 94% pure material, which was carried on to the anion coupling reaction.

D. Acetyl-L-tyrosinyl-L-valyl-N-[1-[2-[(5-phenyl)-1,3,4-oxadiazolyl]carbonyl]-2-(carboxy-t-butyl)-ethyl]-L-alanine amide:

2-Phenyl-1,3,4,-oxadizaole (169 mg, 1.16 mmole) was dissolved in 2 mL dry THF, and chilled to –78 C. n-Butyl lithium (510 uL, 2.5 M solution in hexane) was added via syrringe, after 20 minutes compound C (88 mg, 0.145 mmole) was added via syrringe in 3 mL dry THF and the reaction was allowed to warm to room temperature. After 15 minutes 20 mL of saturated $NH_4Cl$ solution was carefully added under nitrogen, and the solution was rapidly stirred for several minutes. The resulting solution was extracted with EtOAc, dried over $Na_2SO_4$ and concentrated. The resulting product was dissolved in $H_2O/CH_3CN$ and concentrated by freeze-drying. Reverse phase preparative HPLC chromatography (5–60% $CH_3CN$, 0.1% TFA, 30 minute gradient) provided 25.8 mg of a colorless powder upon lyophilization.

E. Acetyl-L-tyrosinyl-L-valyl-N-[1-[2-[(5-phenyl)-1,3,4-oxadiazolyl]carbonyl]-2-carboxy-ethyl]-L-alanine amide:

Compound D (25 mg) was treated with 2 mL of TFA and stirred at room temperature for 2 hours. The TFA was removed on the rotovap, and remaining entrained solvent was removed by adding $CH_2Cl_2$ and $CH_3CN$ and evaporating. The crude product was purified by reverse phase HPLC chromatography (5–60% $CH_3CN$, 0.1% TFA, 30 minute gradient). Lyophilization of appropriate fractions provided 15.7 mg of a colorless lyophilate. Maldi MS M+Na 659 observed. MS FAB $(M+H)^+$637.

1H-NMR: δ 0.77 (m, 6H), 1.1–1.2 (m, 3H), 1.74 (s, 3H) 1.9 (m, 1H), 2.57–2.8 (m, 2H), 2.75–3.34 (m, 2H) 4.14 (m, 1H) 4.3 (m, IH), 4.44 (m, 1H) 5.3 (m, 1H), 6.61 (m, 2H), 7.01 (m, 2H), 7.70 (m, 3H) 7.73 (m, 2H) 7.74–8.00 (m, 2H) 8.1 (m, 2H) 8.78 (m, 1H), 9.13 (bs, 1H) 12.65 (bs, 1H). $^{13}$C-NMR δ 17.8, 17.9, 19.0, 22.3, 30.6, 34.9, 36.3, 47.5, 52.7, 54.0, 57.0, 114.6, 122.3, 127.2, 129.5, 129.9, 132.9, 155.6, 159.6, 164.9, 169.0, 170.2, 171.1, 171.3, 172.2, 172.3, 183.8.

EXAMPLE VI

Acetyl-L-Aspartyl-Valyl-N-[1-[2-[(5-phenyl)-1,3,4-oxadiazolyl] carbonyl]-2-(carboxy)-ethyl]-L-glutamyl amide (CQ-0011)

A. Acetyl-L-Aspartyl(Ot-Bu)-L -Valyl-L-Glutamyl (O-t-Bu)-L-Aspartyl-(O-t-butyl) N-methyl-N-methoxy amide:

Acetyl-Asp(O-t-Bu)-Val-Glu-(O-t-Bu)-OH (0.302 g, 0.586 mmoles, prepared by conventional peptide synthesis) and H-Asp-(O-t-Bu)-N-(CH$_3$)—OCH$_3$ (0.150 g, 0.645 mmole, prepared as in example VIII) were combined in 5mL of DMF and DIEA (305 uL) was added. HBTU (277 mg) was added. After 2 hours an additional 200 uL of DIEA was added and the reaction was allowed to stir approximately 15 hours at room temperature. The reaction was worked up according to method A, dried over Na$_2$SO$_4$ and concentrated to an oil. Preparative reverse phase chromatography (C18, 5–60% CH$_3$CN, 0.1% TFA, 30 minute gradient), and lyophilization of appropriate fractions provided 0.231 g of a colorless lyophilate.

B. Acetyl-L-Aspartyl(O-t-Bu)-Valyl-N-[1-[2-[(5-phenyl)-1,3,4-oxadiazolyl]carbonyl]-2-(carboxy-O-t-butyl)-ethyl]-L-glutamyl(O-t-Bu) amide:

2-Phenyl-1,3,4,-oxadiazole (161 mg, 1.1 mmole) was dissolved in 2 mL dry THF, and chilled to −78° C. n-Butyl lithium (485 uL, 2.5 M solution in hexane) was added via syringe, after 20 minutes compound A (100 mg, 0.138 mmole) was added via syringe in 3 mL dry THF and the reaction was allowed to warm to room temperature. After 60 minutes 20 mL of saturated NH$_4$Cl solution was carefully added under nitrogen, and the solution was rapidly stirred for several minutes. The resulting solution was extracted with EtOAc, dried over Na$_2$SO$_4$ and concentrated. The resulting product was dissolved in H$_2$O/CH$_3$CN and concentrated by freeze-drying. Reverse phase preparative HPLC chromatography (5–60% CH$_3$CN, 0.1% TFA, 30 minute gradient) provided 34 mg of a colorless powder upon lyophilization.

C. Acetyl-L-Aspartyl-Valyl-N-[1-[2-[(5-phenyl)-1,3,4-oxadiazolyl] carbonyl]-2-(carboxy)-ethyl]-L-glutamyl amide:

Compound B (25 mg) was treated with 2 mL mL of TFA and stirred at room temperature for 5.75 hours. The TFA was removed on the rotovap, and remaining entrained solvent was removed by adding CH$_2$Cl$_2$ and CH$_3$CN and evaporating. The crude product was purified by reverse phase HPLC chromatography (5–60% CH$_3$CN, 0.1% TFA, 30 minute gradient). Lyophilization of appropriate fractions provided 15.1 mg of a colorless lyophilate. Maldi MS M+Na 669 observed. MS FAB (M+H)$^+$647.

$^1$H-NMR δ 0.73 (m, 6H), 1.75–1.95 (m, 2H), 1.82 (s, 3H), 1.88 (m, 2H), 2.40–2.70 (m, 2H) 2.75–3.05 (m, 2H), 4.14 (m, 1H), 4.30 (m, 1H), 4.58 (m, 1H), 5.33 (m, 1H) 7.55 (m, 1H) 7.61–7.73 (m, 3H), 8.02 (m, 1H), 8.10 (m, 2H), 8.25 (m, 1H) 8.72–8.82 (m, 1H), 12.3 (bs, 3H). $^{13}$C-NMR δ 17.5, 18.9, 22.3, 27.2, 29.8, 30.6, 34.8, 35.5, 49.3, 51.2, 52.7, 57.0, 122.3, 127.2, 129.5, 132.9, 159.6, 164.9, 169.4, 170.4, 170.5, 171.2, 171.3, 173.7, 183.8.

EXAMPLE VII

General Extractive Work Up Method A

The reaction mixture was diluted with 5–10 volumes of EtOAc and washed three times each with equivalent volumes of 1 N HCl solution, then saturated NaHCO$_3$ solution, and finally with saturated NaCl solution.

EXAMPLE VIII

Inhibitory Activity Against Cathepsin B and L, Papain and Gingipain

The enzyme cathepsin B (E.C. 3.4.22.01) was obtained from Calbiochem (San Diego, Calif.); cathepsin L (E.C. 3.4.22.15) from Athens Research and Technology Inc. (Athens,Ga.); and papain (E.C. 3.4.22.02) from Sigma (St. Louis, Mo.).

Cbz-Phe-Arg-NHMec (—NHMec: 7-(4-methyl) coumarylamide) was obtained from BachemCalifornia, Inc. (Torrance, Calif.). All other reagents were obtained from Sigma.

The enzymes used in enzyme assays with methylcoumarylamides were activated as described elsewhere (Barret, et al., *Methods Enzymol.* 80:535–561 (1981); Brömme, et al., *Biochem. J,* 264: 475–481 (1989). Cathepsin L was assayed in 0.34 M sodium acetate buffer, pH 5.5, containing 0.1% (v/v) Brij 35, 2.5 mM dithiothreitol (DTT) and 5 mM Na$_2$-EDTA. Cathepsin B was assayed under the same conditions, except that the buffer was adjusted to pH 6. Papain was assayed in 50 mM sodium phosphate buffer, pH 6.8, containing 0.2 M sodium chloride, 2 mM DTT, 1 mM Na$_2$-EDTA and 0.025% Brij 35 (v/v).

Initial velocities of enzymatic reactions were measured spectrofluorometrically ($\lambda_{ex}$=370 nm, $\lambda_{em}$ 460 nm) with a Quanta Master QM1 (Photon Technologies International, South Brunswick, N.J.). Stock solutions of the enzymes were diluted into the buffer, equilibrated at room temperature, and preincubated without or with increasing concentrations of inhibitors. The reactions were started by addition of substrate. A total of 4 to 8 inhibitor concentrations were used to determine IC$_{50}$ values. In all cases the substrate concentrations were much smaller than the K$_m$ value, and the IC$_{50}$ values measured approximated the K$_i$ directly (Cheng, et al., Biochemical Pharmacology, 22:3099–3108 (1973)).

Gingipain Assay

All assays were carried out in a 96 well microtiter plate reader and cleavage of BAPNA (Nα-benzoyl-DL-arginine-p-nitroanilide hydrochloride) was detected at 405 nm.

All assays were performed as follows: 180 μl assay buffer (50 mM Tris, 5 nM CaCl$_2$ and 10 nM cysteine, at pH 7.6) was mixed with 10 μl gingipain R (RGP). The mixture was incubated for 5 min. at room temperature to reduce and activate RGP. 10 μl of each inhibitor were added at various concentrations. These mixtures were incubated for 10 min. at room temperature to allow the inhibitors to complex with RGP. 50 μl of 10 mM BAPNA substrate was added. A two minute assay was performed with a final volume of 250 μl, and a final BAPNA concentration of 2 mM.

2 mM BAPNA was sufficient excess of substrate such that substrate depletion did not occur within a 10 minute assay time. For this reason, two minute assays were performed whereby the V$_{max}$ in mOD/min change in absorbance at 405 nm was used as the initial velocity reading. In order to titrate RGP against leupeptin and to determine % activity, these velocity readings were transformed on a percent scale where the 100% control contained no inhibitor. The initial velocity values were also entered into Graphpad Prism regression program along with the various inhibitor concentrations to obtain the IC$_{50}$ values. All data represents the minimum of duplicates, and at times triplicate sets.

Assay results are presented in Table 3. As shown, CM-0019B is an inhibitor of papain and cathepsin L and more selective against cathepsin B than is leupeptin. Compound CQ-0002, which shares the same recognition sequence (Leu-Leu-Arg) with the broad spectrum inhibitor leupeptin, is nearly as potent as leupeptin versus cathepsin B, but surpisingly has a much higher degree of specificity. In addition, compound CQ-0002 inhibits gingipain R with a potency equivalent to that of leupeptin. Compounds CQ-0004 and CQ-0008 are also potent and selective cathepsin L inhibitors.

TABLE 3

$K_i$ [nM] Values for Cysteine Protease Inhibitors

| COMPOUND | PAPAIN | CATHEPSIN B[a] | CATHEPSIN L[a] | GINGIPAIN R[a] |
|---|---|---|---|---|
| Leupeptin | 1.0 ± 0.06 | 6.1 ± 1.2 | 0.62 ± 0.10 | 20.8 (IC50) |
| CM-0019B[b] | 85 | 3,000 | ~100 | |
| CQ-0002 | 1,200 ± 280 | 324 ± 46 | 6.0 ± 0.98 | 28 (IC50) |
| CQ-0004 | 25600 ± 5340 | 27200 ± 1900 | 61 ± 14 | |
| CQ-0008 | 8590 ± 1860 | 1240 ± 182 | 7.13 ± 0.32 | |

[a]Human enzyme.
[b]"B" denotes remake of larger quantities of corresponding CQ number.

EXAMPLE IX

Inhibitory Activity Against Caspases

Assay for ICE Inhibition

To examine the ability of the caspase family inhibitors, CQ-0010 and CQ-0011, to inhibit human IL-1β production, two different assays were employed. In the first, the human monocytic cell line, THP-1, was stimulated with *E. coli* lipopolysaccharide (LPS serotype 0127-88; Sigma Chemical Co., St. Louis, Mo.) in the presence and absence of the inhibitors. This cell line synthesizes and secretes IL-1β and TNFα as well as other cytokines upon LPS stimulation. The second assay used freshly-isolated human whole blood similarly stimulated with LPS.

THP-1 Assay

Two×10⁶ THP-1 cells were added to 24 well plates in 1 ml RPMI supplemented with 1% FCS, glutamine and 5×10⁻⁵ M mercaptoethanol. Two-fold serial dilutions of the inhibitors, CQ-0010, CQ-0011 and the commmercially available Ac-YVAD-CHO (Biomol Research Laboratories Inc., Plymouth Meeting, Pa.), were preincubated with the cells for 15 min at 37° C. LPS was then added to a final concentration of 1 ug/ml and the plates incubated for 4 hr at 37° C. All incubations were carried out in a humidified incubator with 5% $CO_2$ in air.

Supernatants were harvested after 4 hr and assayed by ELISA for the presence of TNFα and IL-1β using commercially available kits (PerSeptive Biosystems, Framingham, Mass. and R&D Systems, Minneapolis, Minn., respectively).

Human Whole Blood Assay

Heparinized whole blood (19.7 U heparin per ml) from healthy volunteers was collected and dispensed into 12×75 mm polystyrene tubes (0.25 ml per tube). The inhibitors, CQ-0010, CQ-0011 and Ac-YVAD-CHO were dissolved in DMSO, then diluted and added to the tubes in 0.25 ml and preincubated with the blood for 15 min at 37° C. LPS was then added to a final concentration of 10 or 100 ug/ml.

The tubes were loosely-capped and incubated in a water bath for 4 hr at 37° C. after which they were immersed briefly in an ice-water bath. Supernatants were harvested by centrifngation and stored at −70° C. The presence of TNFα and IL-1β was detected by commercially-available ELISA kits.

Assay for Other Caspase and Granzyme B Inhibition

Inhibition constants were measured photometrically for YAMA (caspase 3), Lap3 (caspase 7), FLICE (caspase 8), Mch2 (caspase 6) and granzyme B. The buffer used for all enzymes consisted of 50 mM Hepes, 100 mM sodium chloride, 10% (v/v) sucrose, 0.1% (v/v) CHAPS and 10 mM dithiothreitol (DTT). In the case of granzyme B, only 1 mM DTT was used.

Enzymes were incubated at 37° C. for 10 minutes in 100 μL well plates and synthetic substrate and inhibitor were added simultaneously. Final substrate concentration was 20 μM in all cases. The synthetic substrate Ac-DEVD-pNA was used for all caspases and Succ-AAPD-pNA was used for granzyme B. The appearance of product was monitored over 10 minutes at 410 nm using a Spectromax 340 and $IC_{50}$ curves were calculated from the initial slopes at varying inhibitor concentrations and inhibition constants were calculated.

The results are shown in Table 4.

TABLE 4

Inhibition of Caspases - Comparison with Ac-YVAD-CHO

| Caspases | Ac-YVAD-CHO | Ac-YVAD-het (CQ-0010) | Ac-DVED-het (CQ-0011) |
|---|---|---|---|
| YAMA (CPP32, Caspase 3) | 20 | 3.3 | ≦0.1 |
| Mch2 (Caspase 6) | 100 | 33 | 6.7 |
| Lap3 (Mch3, Caspase 7) | Not Active | Not Active | ≦0.03 (slow) |
| FLICE (Mch5, Caspase 8) | 3.7 | ≦0.02 | ≦0.03 (slow) |
| ICE (Caspase 1) | 0.3[b] 0.3–0.5[c] | 0.3[b] 0.3–0.5[c] | 3[b] |
| Granzyme | Not Active | Not Active | Not Active |

[a]Values given are $K_i$ in μM, unless otherwise indicated.
[b]IC50 (μM) values of reduction of IL-1β release from THP-1 cell line.
[c]IC50 (μM) values of reduction of IL-1β release in whole blood assay.

The results indicate that CQ-0010 is an extremely potent and specific inhibitor of IL-1β production, capable of almost completely inhibiting the production of this cytokine at 5 μM (FIG. 1) while having no dose-dependent effect on levels of TNFα produced (results not shown). The $IC_{50}$ of CQ-0010 was estimated from these dose curves to be 0.3 μM. CQ-0011 also inhibited IL1β production but with approximately 10-fold less potency (FIG. 1; Table 4).

Figure 2:
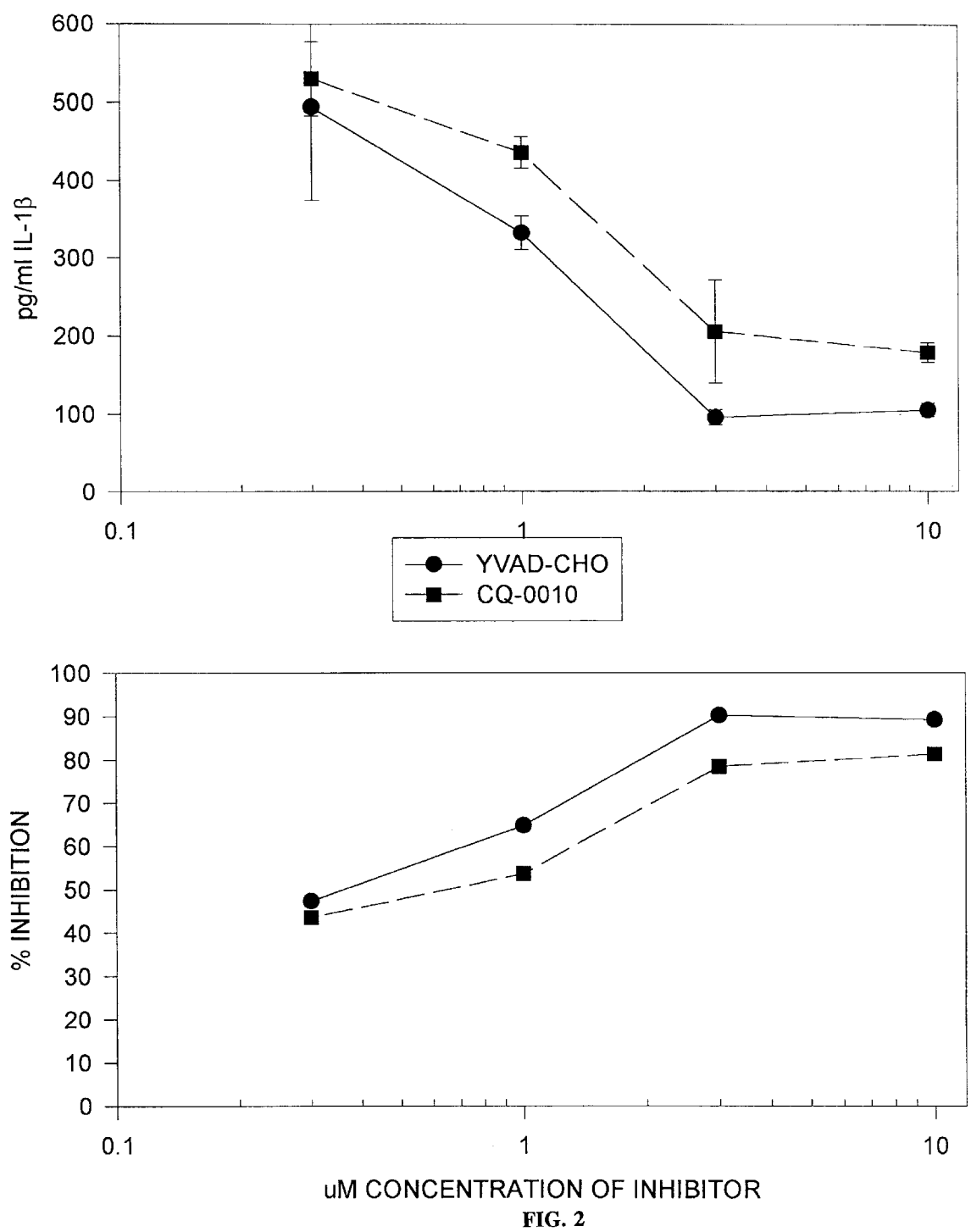
FIGS. 2A and 2B show the inhibition of the production of mature IL-1β in whole blood by certain compounds of the present invention.
Figure 3:
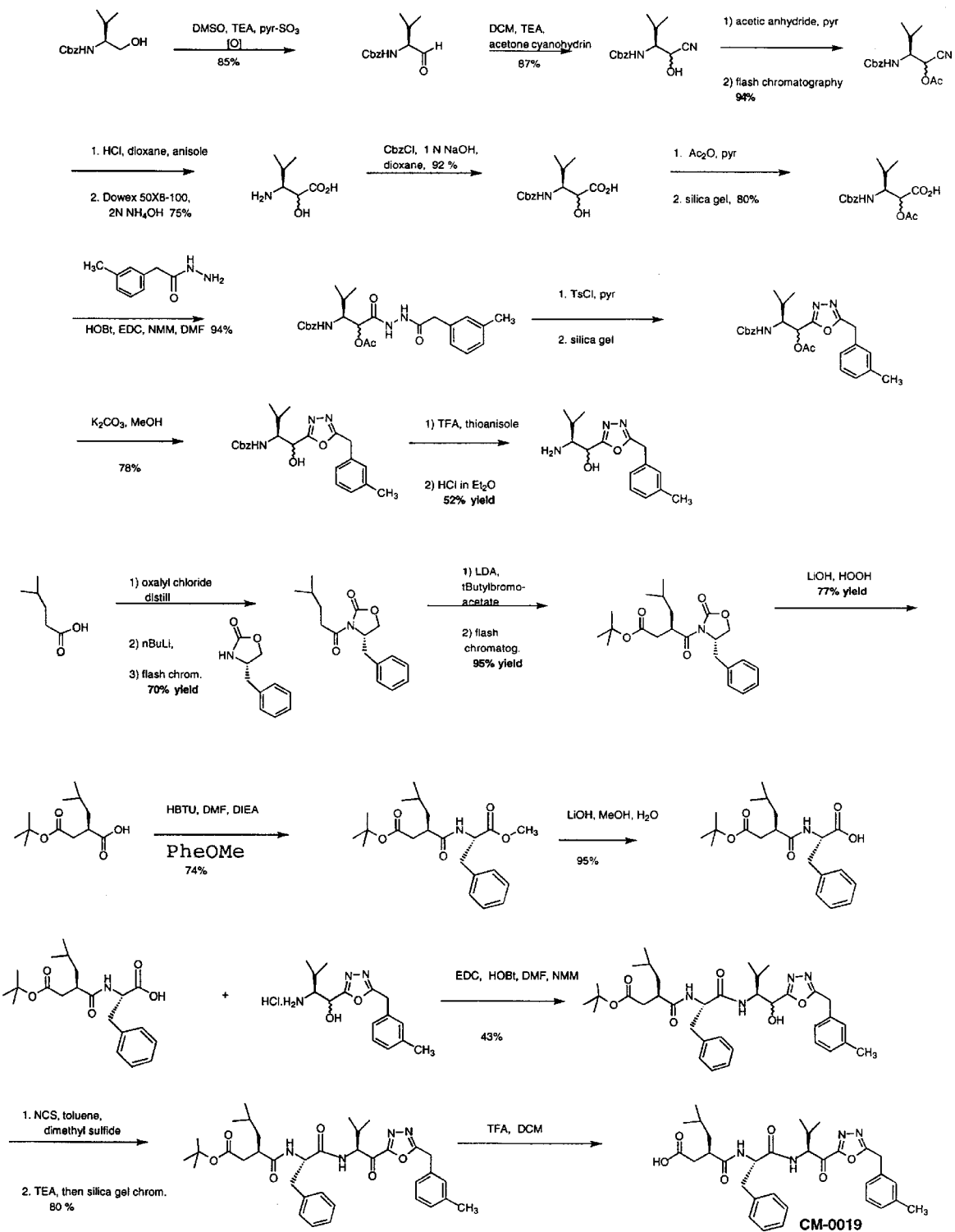
FIG. 3 is a schematic representation of the synthesis of a compound according to the invention (CM-0019).

In the whole blood assay, CQ-0010 was again equipotent to Ac-YVAD-CHO with an $IC_{50}$ of 0.3–0.5 μM (FIGS. 2a and b).

It should be noted that CQ-0010 was equipotent to the aldehyde equivalent (Ac-YVAD-CHO) in inhibiting ICE, but showed improved inhibition against FLICE with a $K_i$ of ≦20 nM.

Compound CQ-0011 is a potent inhibitor of Lap3 and FLICE. The compounds are selective and potent caspase inhibitors as shown by their inactivity with respect to granzyme B.

We claim:

1. A cysteine protease inhibitor of formula (I):

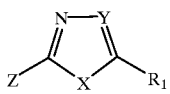

wherein Z is a peptide or peptide mimetic cysteine protease binding moiety having between 2 and 5 amino acid residues or amino acid mimetics for between 1 and 5 amino acid residues, wherein the sum of the amino acid residues and the amino acid residues for which there is one or more amino acid mimetics is between 2 and 5 and the cysteine protease binding moiety is capable of binding to a cysteine protease;

$R_1$ is alkyl or alkenyl, optionally substituted with 1–3 halo or hydroxy, alkylamino, dialkylamino, alkyldialkylamino, or cycloalkyl, alkylcycloalkyl, alkenylcycloalkyl, $(C_5-C_{12})$ aryl; $(C_5-C_{12})$arylalkyl or$(C_5-C_{12})$arylalkenyl, wherein the aryl groups of the arylalky or arylalkenyl comprises 0–4 heteroatoms selected from N, O and S, and are optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamide, $(C_5-C_6)$aryl, —O—$(C_5-C_6)$aryl, arylcarboxamide, alkylthio or haloalkylthio; and one of Y and X is O and the other is N, said N being optionally substituted with alkyl or alkenyl optionally substituted with 1–3 halo atoms; $(C_5-C_6)$ aryl, arylalkyl or arylalkenyl optionally comprising 1–3 heteroatoms selected from N, O and S, and optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamide, arylcarboxamide, alkylthio or haloalkylthio;

wherein at least one of Y or X is N; or a pharmaceutically acceptable salt thereof.

2. An inhibitor of claim 1 wherein Z is of the formula (II):

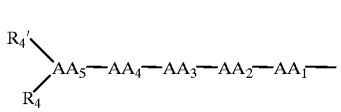

(II)

wherein $AA_1, AA_2, AA_3, AA_4$ and $AA_5$ are independently an amino acid residue or amino acid residue mimetic; a direct bond or absent; and $R_4$ and $R_4'$ are independently —C(O)$R_5$, —C(O)NHR$_5$, —S(O)$_2$R$_5$, —C(O)OR$_5$, —CR$_5$ or R$_5$, where R$_5$ is H, alkyl, alkenyl or alkynyl optionally substituted with halo, cyano, nitro, haloalkyl, amino, aminoalkyl, dialkylamino, haloalkoxy, carboxyl, carboalkoxy or alkylcarboxamide; cycloalkyl, alkylcycloalkyl, $(C_5-C_{12})$ aryl or $(C_5-C_{12})$arylalkyl optionally comprising 1–4 heteroatoms selected from N, O and S, and optionally substituted with halo, cyano, nitro, haloalkyl, amino, aminoalkyl, dialkylamino, haloalkoxy, carboxyl, carboalkoxy, alkylcarboxamide, alkyl, alkenyl, alkynyl or $(C_5-C_{12})$aryl; or absent; or together $R_4$ and $R_4'$ form a ring comprising 5–7 atoms selected from C, N, S and O.

3. An inhibitor of claim 2 wherein the cysteine protease binding moiety comprises (i) amino acids, (ii) amino acids and amino acid mimetics, or (iii) amino acid mimetics, wherein the moiety corresponds to a peptide of 5 amino acid residues.

4. An inhibitor of claim 2 wherein the cysteine protease binding moiety comprises (i) amino acids, (ii) amino acids and amino acid mimetics, or (iii) amino acid mimetics, wherein the moiety corresponds to a peptide of 4 amino acid residues.

5. An inhibitor of claim 2 wherein the cysteine protease binding moiety comprises a (i) amino acids, (ii) amino acids and amino acid mimetics, or (iii) amino acid mimetics wherein the moiety corresponds to a peptide of 3 amino acid residues.

6. An inhibitor of claim 2 wherein the cysteine protease binding moiety comprises a (i) amino acids, (ii) amino acids and amino acid mimetics, or (iii) amino acid mimetics wherein the moiety corresponds to a peptide of 2 amino acid residues.

7. An inhibitor of claim 2 wherein the amino acids are selected from argim ine or an arginine mimetic, proline; aspartic and glutamic acid and the aryl and alkyl esters thereof; alanine and glycine optionally substituted at the α-carbon or α-nitrogen with alkl, cycloalkyl or aryl; leucine, isoleucine; cysteine optionally substituted at the sulfur atom with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; phenylalanine, homo-phenylalanine, dehydro-phenylalanine, indoline-2-carboxylic acid; tetrahydroisoquinoline-2-carboxylic acid optionally substituted with halo, cyano, nitro, haloalkyl, amino, aminoalkyl, dialkylarino, alkyl, alkoxy, haloalkoxy, carboxyl, carboalkoxy, alkylcarboxamide, arylcarboxamide, alkylthio or haloalkylthio; tyrosine, serine or threonine optionally substituted with alkyl or aryl; tryptophan, histidine, methionine, valine, norvaline, norleucine, octahydroindole-2-carboxylic acid; asparagine, glutamine and lysine optionally substituted at the nitrogen atom with alkyl, alkenyl, alkynyl, alkoxyalkyl, alkylthioalkyl, alkylaminoalkyl, dialkylaminoalkyl, carboxyalkyl, alkoxycarbonyl alkyl or cycloalkyl, bicycloalkyl, cycloalkyl alkyl, bicycloalkyl alkyl or fused aryl-cycloalkyl alkyl optionally comprising 1 or more heteroatoms selected from N, O and S.

8. An inhibitor of claim 2 wherein $AA_1$ is of the formula (IIIa):

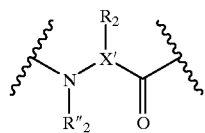
(IIIa)

wherein X' is CR$_2$' or N; and

R$_2$, R$_2$' and R$_2$" are independently H; alkyl or alkenyl optionally substituted with 1–3 halo, hydroxy, thio, alkylthio, amino, alkylamino, dialkylamino, alkylguanidinyl, dialkylguanidinyl, guanidinyl; —RCOR', —RCOOR', —RNR'R"R° or —RC(O)NR'R" where R is alkyl or alkenyl, and R', R" and R° are independently H, alkyl, alkenyl, cycloalkyl or (C$_5$–C$_6$)aryl; or cycloalkyl, alkylcycloalkyl, alkenylcycloalkyl, alkyl-oxyaryl, alkyl-thioaryl, (C$_5$–C12) aryl, (C$_5$–C$_{12}$)arylalkyl or (C$_5$–C$_{12}$) arylalkenyl optionally comprising 1–4 heteroatoms selected from N, O and S, and optionally substituted with hydroxy, halo, cyano, nitro, haloalkyl, amino, aminoalkyl, dialkylamino, amidine, alkylamidine, dialkylamidine, alkyl, alkenyl, alkynyl, alkoxy, haloalkoxy, carboxyl, carboalkoxy, alkylcarboxamide, (C$_5$–C$_6$)aryl, —O—(C$_5$–C$_6$)aryl, arylcarboxamide, alkylthio or haloalkylthio; or R$_2$ and R$_2$' together with X' form a ring comprising 4–7 atoms selected from C, N, S and O, said ring optionally subsititued with hydroxy, halo, cyano, nitro, haloalkyl, amino, aminoalkyl, dialkylamino, amidine, alkylamidine, dialkyl amidine, allyl, alkenyl, alkynyl, alkoxy, haloalkoxy, carboxyl, carboalkoxy, alkylcarboxamide, (C$_5$–C$_6$)aryl, —O—(C$_5$–C$_6$)aryl, arylcarboxamide, alkylthio or haloalkylthio.

9. An inhibitor of claim 8 wherein AA$_2$ is of the formula (IIIb):

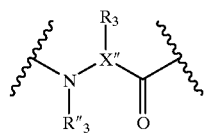
(IIIb)

or selected from a compound of formulas IV to XXV:

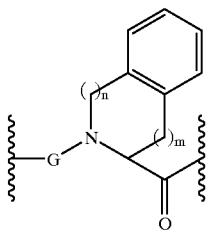
(IV)

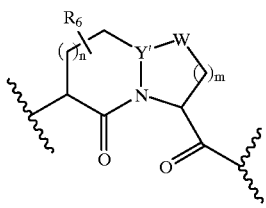
(V)

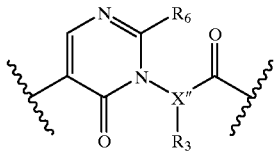
(VI)

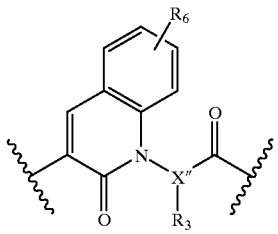
(VII)

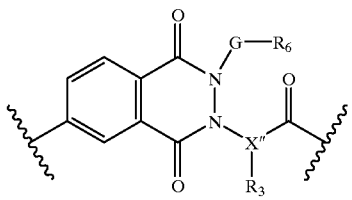
(VIII)

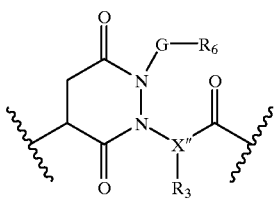
(IX)

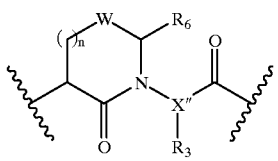
(X)

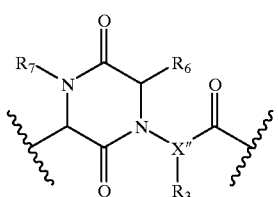
(XI)

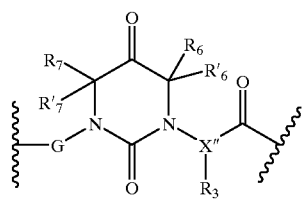
(XII)
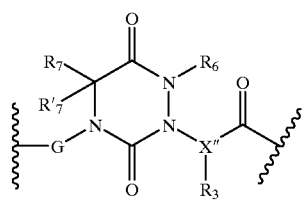
(XIII)
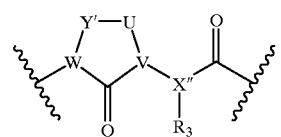
(XIV)
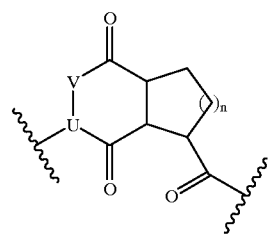
(XV)
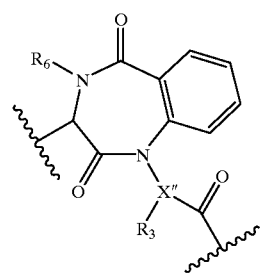
(XVI)
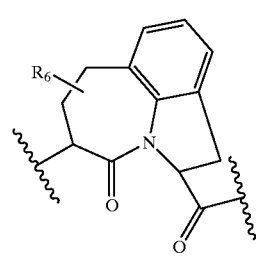
(XVII)
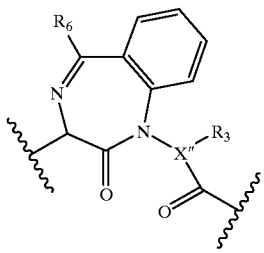
(XVIII)
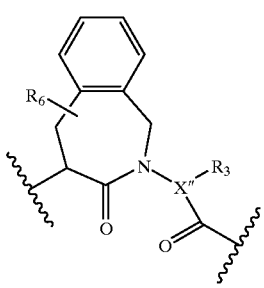
(XIX)
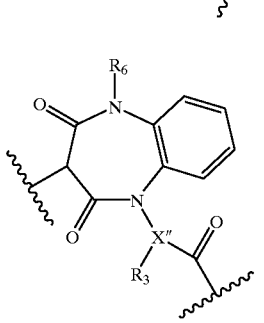
(XX)
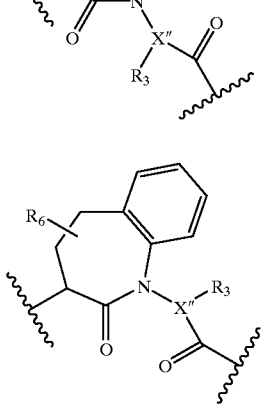
(XXI)
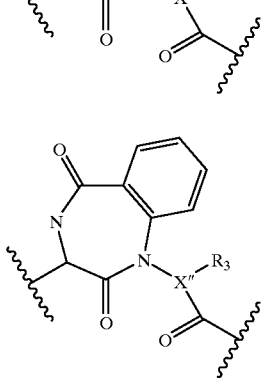
(XXII)
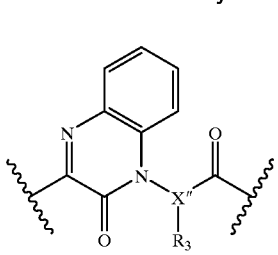
(XXIII)

-continued (XXIV)

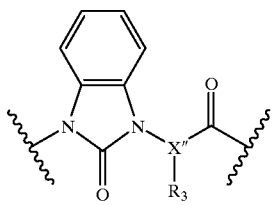

wherein X" is CR'$_3$ or N;

R$_3$, R'$_3$ and R"$_3$ are independently H; alkyl or alkenyl optionally substituted with 1–3 halo, hydroxy, thio, alkylthio, amino, alkylamino, dialkylamino, alkylguanidinyl, dialkylguanidinyl, guanidinyl; —RCOR', —RCOOR' or —RC(O)NR'R" where R is alkyl or alkenyl, and R' and R" are independently H, alkyl, alkenyl, cycloalkyl or (C$_5$–C$_6$)aryl; or cycloalkyl, alkylcycloalkyl, alkenylcycloalkyl, alkyl-oxyaryl, alkyl-thioaryl, (C$_5$–C$_{12}$) aryl, (C$_5$–C$_{12}$)arylalkyl or (C$_5$–C$_{12}$)arylalkenyl optionally comprising 1–4 heteroatoms selected from N, O and S, and optionally substituted with hydroxy, halo, cyano, nitro, haloalkyl, amino, aminoalkyl, dialkylamino, amidine, alkylamidine, dialkylamidine, alkyl, alkenyl, alkynyl, alkoxy, haloalkoxy, carboxyl, carboalkoxy, alkylcarboxamide, (C$_5$–C$_6$)aryl, —O—(C$_5$–C$_6$)aryl, arylcarboxamide, alkylthio or haloalkylthio;

m is 0, 1 or 2;

n is 0, 1 or 2;

G is —C(O)—, —NHC(O)—, —S(O)$_2$—, —OC(O)—, —C— or a direct bond;

R$_6$, R$_7$, R'$_6$, R'$_7$ are independently H, alkyl, alkenyl, halo, alkoxy, carboxyl, carboalkoxy, amino, aminoalkyl, dialkylamino; cycloalkyl, (C$_5$–C$_6$) aryl or (C$_5$–C$_6$) arylalkyl optionally comprising 1–3 heteroatoms selected from N, O and S, and optionally substituted with alkyl, alkenyl, alkynyl, halo, cyano, nitro, haloalkyl, haloalkoxy, amino, alkylamino, dialkylamino, alkoxy, haloalkoxy, carboxyl, carboalkoxy, alkylcarboxamide, alllylthio, guanidine, alkylguanidine, dialkylguanidine, amidine, alkylamidine or dialkylamidine; and U, V, W and Y' are independently or together N, C, C(O), N(R$_9$) where R$_9$ is H, alkyl, halo, alkoxy, carboalkoxy, cycloalkoxy, carboxyl, alkylthio, amino, alkylamino, dialkylamino, or aryl, fused aryl or cycloalkyl optionally comprising 1 or more heteroatoms selected from O, S and N, and optionally subsituted with halo or alkyl; N(R$_{10}$) where R$_{10}$ is H, alkyl, alkenyl or cycloalkyl, aryl, arylalkyl or fused aryl-cycloalkyl optionally comprising 1–4 heteroatoms selected from N, O and S, and optionally substituted with alkyl, alkenyl, aLkynyl, halo, cyano, nitro, haloalkyl, haloalkoxy, amino, alkylamino, dialkylamino, alkoxy, haloalkoxy, carboxyl, carboalkoxy, alkylcarboxamide, alkylthio, guanidine, alkylguanidine, dialkylguanidine, amidine, alkylamidine or dialkylamidine; or C(R$_{11}$) (R$_{12}$) where R$_{11}$ and R$_{12}$ are independently or together H, alkyl, alkythio, alkythioalkyl or cycloalkyl, alkylcycloalkyl, phenyl or phenyl alkyl optionally subsituted with guanidine, carboalkoxy, hydroxy, haloalkyl, alkylthio, alkylguanidine, dialkylguanidine, amidine, alkylamidine or dialkylamidine.

10. An inhibitor of claim 9 wherein AA$_3$, AA$_4$ and AA$_5$ are a direct bond or absent; or an amino acid selected from arginine or an arginine mimetic, proline; aspartic and glutamic acid and the aryl and alkyl esters thereof; alanine or glycine optionally substituted at the α-carbon or α-nitrogen with alkyl, cycloalkyl or aryl; leucine, isoleucine; cysteine optionally substituted at the sulfur atom with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; phenylalanine, homo-phenylalanine, dehydro-phenylalanine, indoline-2-carboxylic acid; tetrahydroisioquinoline-2-carboxylic acid optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; tyrosine, serine or threonine optionally substituted with alkyl or aryl; tryptophan, histidine, methionine, valine, norvaline, norleucine, octahydroindole-2-carboxylic acid; asparagine, glutamine and lysine optionally substituted at the nitrogen atom with alkyl, alkenyl, alkynyl, alkoxyalkyl, alkylthioalkyl, alkylaminoalkyl, dialkylaminoalkyl, carboxyalkyl, alkoxycarbonyl alkyl or cycloalkyl, bicycloalkyl, cycloalkyl alkyl, bicycloalkyl alkyl or fused aryl-cycloalkyl alkyl optionally comprising 1 or more heteroatoms selected from N, O and S.

11. An inhibitor of claim 8 wherein X' is N.

12. An inhibitor of claim 9 wherein X" is N.

13. An inhibitor of claim 8 wherein X' is CR'$_2$, and R'$_2$ is H.

14. An inhibitor of claim 9 wherein X" is CR'$_3$, and R'$_3$ is H.

15. An inhibitor of claim 10 wherein Z is a calpain binding moiety.

16. An inhibitor of claim 15 wherein R$_2$ is CH$_3$SCH$_2$CH$_2$—, HOOC(CH$_2$)$_2$CH$_2$—, cyclohexyl-CH$_2$—, imidazolyl-CH$_2$, (CH$_3$)$_2$CHCH$_2$—, (CH$_3$)$_2$CH—, CH$_3$CH$_2$CH$_2$— or CH$_3$(CH$_2$)$_2$CH$_2$—; benzyl optionally substituted with alkoxy, OH or —O-benzyl; H$_2$NC(=$^+$NH$_2$) NHCH$_2$CH$_2$CH$_2$—; —R'—C(=$^+$NH$_2$)NH$_2$; —R'—NHC(=$^+$ NR")NR°; or —R'—NR"R° where R' is cycloalkyl, aryl or arylalkyl optionally substituted with one or more heteroatoms selected from N, S or O alkyl; and R" and R° are alkyl or cycloalkyl.

17. An inhibitor of claim 16 wherein R$_3$ is —CH$_2$-benzyl, benzyl, (CH$_3$)$_3$C—, (CH$_3$)$_3$CCH$_2$—, (CH$_3$)$_2$CH—, CH$_3$(CH$_2$)$_2$CH$_2$—, CH$_3$CH$_2$CH(CH$_3$)— or (CH$_3$)$_2$CHCH$_2$—.

18. An inhibitor of claim 17 wherein R$_5$ is benzyl, isoquinolinyl, quinolinyl, naphthyl or HOOCCH$_2$C(CH$_2$CH (CH$_3$)$_2$)—.

19. An inhibitor of claim 17 wherein R$_4$ is Cbz wherein the phenyl is optionally substituted with nitro.

20. An inhibitor of claim 17 wherein R$_4$ is toluenesulfonyl, methanesulfonyl, FMOC or (+)-menthyloxy-CO—.

21. An inhibitor of claim 16 wherein AA$_3$ is leucine, AA$_4$ and AA$_5$ are direct bonds or absent, and R$_5$ is alkyl.

22. An inhibitor of claim 7 wherein Z is

R$_4$—Leu—Leu—Leu—;

R$_4$—Leu—Leu—;

R$_4$—Leu—Leu—Phe—;

R$_4$—Leu—Abu—;

R$_4$—Val—Phe—;

R$_4$—Leu—Leu—Nle—;

R$_4$—Ala—t—BuGly—Val—;

R$_4$—t—BuGly—Val—;

R$_4$—Leu—Leu—Met—; or $R_4$—Leu—Nle—.

23. An inhibitor of claim 7 wherein Z is Cbz—Leu—Nle—; or Cbz—Leu—Val—.

24. An inhibitor of claim 10 wherein Z is a cysteine cathepsin binding moiety.

25. An inhibitor of claim 24 wherein $R_2$ is $CH_3$—, $(CH_3)_2CH$—, $(CH_3)_2CHCH_2$—, $CH_3(CH_2)_2CH_2$—, $CH_3CH(\text{—O-benzyl})$— or benzyl—S—$CH_2$—; benzyl or —$CH_2$-benzyl optionally substituted with OH or —OR' where R' is alkyl or aryl; $H_2NC(=^+NH_2)NHCH_2CH_2CH_2$—; —R'—$C(=^+NH_2)NH_2$; —R'—$NHC(=^+NR")NR°$; or —R'—NR"R° where R' is cycloalkyl, aryl or arylalkyl optionally substituted with one or more heteroatoms selected from N, S or O alkyl; and R" and R° are alkyl or cycloalkyl.

26. An inhibitor of claim 25 wherein $R_3$ is H, $(CH_3)_2CH$—, $(CH_3)_2CHCH_2$—, $CH_3(CH_2)_2CH_2$—, benzyl optionally substituted with hydroxy and halo; (naphthyl)—$CH_2$—; $H_2N(CH_2)_3CH_2$—, $H_2N(CH_2)_2CH_2$—, $H_2NC(=^+NH_2)NHCH_2CH_2CH_2$—; —R'—$C(=^+NH_2)NH_2$; —R'—$NHC(=^+NR")NR°$; or —R'—NR"R° where R' is cycloalkyl, aryl or arylalkyl optionally substituted with one or more heteroatoms selected from N, S or O alkyl; and R" and R° are alkyl or cycloalkyl.

27. An inhibitor of claim 24 wherein Z is a cathepsin B binding moiety.

28. An inhibitor of claim 27 wherein $R_2$ and $R_3$ are independently benzyl, —$CH_2$-benzyl, $H_2N(CH_2)_3CH_2$—, $H_2N(CH_2)_2CH_2$—, $H_2NC(=^+NH_2)NHCH_2CH_2CH_2$—; —R'—$C(=^+NH_2)NH_2$; —R'—$NHC(=^+NR")NR°$; or —R'—NR"R° where R' is cycloalkyl, aryl or arylalkyl optionally substituted with one or more heteroatoms selected from N, S or O alkyl; and R" and R° are alkyl or cycloalkyl.

29. An inhibitor of claim 27 or 28 wherein $AA_3$ is Ile or Leu.

30. An inhibitor of claim 28 wherein —$AA_2$—$AA_1$— are
   —Phe—hPhe—;
   —Arg—hPhe—;
   —Arg mimetic—hPhe—;
   —Lys—hPhe—; or
   —Orn—hPhe.

31. An inhibitor of claim 24 wherein Z is a cathepsin L, O, K, or H binding moiety.

32. An inhibitor of claim 31 wherein Z is a cathepsin L binding moiety.

33. An inhibitor of claim 32 wherein $R_3$ is benzyl or $(CH_3)_2CHCH_2$—.

34. An inhibitor of claim 32 or 33 wherein $R_2$ is —$CH_2$-benzyl.

35. An inhibitor of claim 24 wherein Z is a cathepsin S binding moiety.

36. An inhibitor of claim 35 wherein $R_2$ and $R_3$ are alkyl.

37. An inhibitor of claim 36 wherein $R_2$ and $R_3$ are independently $(CH_3)_2CH$—, $(CH_3)_2CHCH_2$— or $CH_3(CH_2)_2CH_2$—.

38. An inhibitor of claim 35 wherein $R_3$ is benzyl, $(CH_3)_2CHCH_2$— or $(CH_3)_2CH$—.

39. An inhibitor of claim 35 or 38 wherein $R_2$ is —$CH_2$-benzyl.

40. An inhibitor of claim 39 wherein $AA_3$, $AA_4$ and $AA_5$ are direct bonds or absent.

41. An inhibitor of claim 40 wherein $R_5$ is benzyl, isoquinolinyl, quinolinyl, naphthyl or $HOOCCH_2C(CH_2CH(CH_3)_2)$—.

42. An inhibitor of claim 41 wherein R is Cbz.

43. An inhibitor of claim 31 wherein Z is a cathepsin H binding moiety.

44. An inhibitor of claim 43 wherein Z is
   $R_4$—hPhe—; or
   HCl•hPhe—.

45. An inhibitor of claim 31 wherein Z is a cathepsin K binding moiety.

46. An inhibitor of claim 45 wherein $R_3$ is benzyl, $(CH_3)_2CHCH_2$— or $(CH_3)_2CH$—.

47. An inhibitor of claim 45 or 46 wherein $AA_3$ is Gly; and $AA_4$ is Val or D—Val.

48. An inhibitor of claim 7 wherein Z is a cathepsin K binding moiety; and
   $AA_1$ is Arg, Arg mimetic or hPhe;
   $AA_2$ is Pro;
   $AA_3$ is Gly; and
   $AA_4$ is Val or D—Val.

49. An inhibitor of claim 7 wherein Z is a cathepsin K binding moiety; and is
   $R_4$—Pro—$AA_1$—;
   $R_4$—Gly—Pro—$AA_1$—;
   $R_4$—Val—Gly—Pro—$AA_1$;
   D—Val—Gly—Pro—$AA_1$—; or
   $R_4$—D—Val—Gly—Pro—$AA_1$; where
   $AA_1$ is Apa, Arg or Arg mimetic, or hphe.

50. An inhibitor of claim 24 wherein Z is
   $R_4$—$AA_3$—Leu—hPhe—;
   $R_4$—$AA_3$—Phe—hPhe—; or
   $R_4$—$AA_3$—Val—hPhe—;
   where $AA_3$ is Gly, Val, D—Val, a direct bond or absent.

51. An inhibitor of claim 24 wherein Z is Mu—Val—hPhe—.

52. An inhibitor of claim 10 wherein Z is a caspase binding moiety.

53. An inhibitor of claim 52 wherein $R_2$ is —RCOOR'.

54. An inhibitor of claim 53 wherein R is —$CH_2$— and R' is H.

55. An inhibitor of claim 53 wherein $AA_3$ and $AA_4$ are amino acid residues and $AA_5$ is a direct bond.

56. An inhibitor of claim 55 wherein Z is an interleukin-1β converting enzyme binding moiety.

57. An inhibitor of claim 56 wherein $AA_4$ is optionally substituted tyrosine or leucine.

58. An inhibitor of claim 57 wherein $AA_3$ is valine, glutamate or an ester thereof.

59. An inhibitor of claim 58 wherein $R_3$ is —$CH_3$ or $(CH_3)_2CH$—.

60. An inhibitor of claim 56 wherein $R_3$ is —$CH_3$ or imidazolyl—$CH_2$—; $AA_3$ is valine or glutamate; and $R_5$ is —$CH_3$.

61. An inhibitor of claim 7 wherein Z is an interleukin-1β converting enzyme binding moiety, and is
   $R_4$—$AA_5$—$AA_4$—$AA_3$—Pro—$AA_1$; where $AA_1$ is Asp or Asp ester.

62. An inhibitor of claim 61 wherein —$AA_5$—$AA_4$—$AA_3$— is
   —Ala—;
   —Glu—;
   —Val—;
   —Tyr—Ala—;
   —Tyr—Glu—;
   —Tyr—Val—;
   —Leu—Ala—;

—Leu—Glu—; or

—Leu—Val—.

63. An inhibitor of claim 10 wherein Z is an interleukin-1β converting enzyme binding moiety and $AA_2$ is of the formula (VI);

wherein X" is $CR'_3$;

$R_2$ is —RCOOR' where R is alkyl or alkenyl, and R' is H, alkyl, alkenyl, cycloalkyl or ($C_5$-$C_6$) aryl.

64. An inhibitor of claim 63 wherein $R_3$ and $R'_3$ are H.

65. An inhibitor of claim 63 wherein $AA_3$, $AA_4$ and $AA_5$ are direct bonds or absent, and $R_2$ is —RCOOH where R is —$CH_2$—.

66. An inhibitor of claim 65 wherein $R_6$ is phenyl or benzyl substituted with halo.

67. An inhibitor of claim 66 wherein $R_5$ is benzyl, isoquinolinyl, quinolinyl, naphthyl or HOOCCH$_2$C(CH$_2$CH(CH$_3$)$_2$)—.

68. An inhibitor of claim 53 wherein Z is a YAMA binding moiety, where R is —$CH_2$— and $AA_4$ is Asp or an ester thereof.

69. An inhibitor of claim 68 wherein $AA_3$ is optionally substituted glutamine, or glutamic acid or an ester thereof.

70. An inhibitor of claim 69 wherein $R_2$ is (CH$_3$)$_2$CH— or CH$_3$SCH$_2$CH$_2$—.

71. An inhibitor of claim 53 wherein Z is a FLICE binding moiety, where $R_2$ is —$CH_2$— and $AA_4$ is optinally substituted lysine.

72. An inhibitor of claim 71 wherein $AA_3$ is glutamic acid.

73. An inhibitor of claim 72 wherein $R_3$ is (CH$_3$)$_2$CH—.

74. An inhibitor of claim 10 wherein Z is a viral or microbial cysteine protease binding moiety.

75. An inhibitor of claim 74 wherein Z is a gingipain binding moiety.

76. An inhibitor of claim 75 wherein Z is a gingipain K binding moiety.

77. An inhibitor of claim 76 wherein $R_2$ is RNR'R"R° where R' is H; R" and R° are H or alkyl.

78. An inhibitor of claim 75 wherein Z is a gingipain R binding moiety.

79. An inhibitor of claim 78 wherein $R_2$ is H$_2$NC(=$^+$NH$_2$)NHCH$_2$CH$_2$CH$_2$—; —R'—C(=$^+$NH$_2$)NH$_2$; —R'—NHC(=$^+$NR")NR°; or —R'—NR"R° where R' is cycloalkyl, aryl or arylalkyl optionally substituted with one or more heteroatoms selected from N, S or O alkyl; and R" and R° are alkyl or cycloalkyl.

80. An inhibitor of claim 7 wherein Z is a gingipain binding moiety, and $AA_2$ is proline.

81. An inhibitor of claim 80 wherein Z is $R_4$—Leu—Pro—$AA_1$—, where $AA_1$ is arginine or an arginine mimetic.

82. An inhibitor of claim 74 wherein Z is a human coronavirus protease binding moiety, and $R_2$ is H$_2$NC(=$^+$NH$_2$)NHCH$_2$CH$_2$CH$_2$—; —R'—C(=$^+$NH$_2$)NH$_2$; —R'—NHC(=$^+$NR")NR°; or —R'—NR"R° where R' is cycloalkyl, aryl or arylalkyl optionally substituted with one or more heteroatoms selected from N, S or O alkyl; and R" and R° are alkyl or cycloalkyl.

83. An inhibitor of claim 82 wherein $R_3$ is (CH$_3$)$_2$CH—, (CH$_3$)$_2$CHCH$_2$— or CH$_3$(CH$_2$)$_2$CH$_2$—;

$AA_3$ is Asp or an ester thereof; Leu, Arg or Arg mimetic, or direct bond;

$AA_4$ and $AA_5$ are direct bonds or absent; and $R_5$ is alkyl.

84. An inhibitor of claim 74 wherein Z is a hepatitis A virus 3C proteinase binding moiety, and $R_2$ is —RC(O)NR'R" where R' and R" are H or —CH$_3$; or RCOOR' where R' is CH$_3$; and $AA_3$ and $AA_4$ are amino acid residues.

85. An inhibitor of claim 84 wherein $AA_4$ is Leu.

86. An inhibitor of claim 85 wherein $R_3$ is —CH$_3$ and $AA_3$ is Ala.

87. An inhibitor of claim 7 wherein Z is a hepatitis A virus 3C proteinase binding moiety, and is $R_4$—Leu—$AA_3$—Thr—Gln—;

$R_4$—Trp—$AA_3$—Thr—Gln—;

$R_4$—Val—$AA_3$—Thr—Gln—;

$R_4$—Ile—$AA_3$—Thr—Gln—; or $R_4$—D—Leu—$AA_3$—Thr—Gln—;

where $AA_3$ is Arg or Arg mimetic.

88. An inhibitor of claim 74 wherein Z is an Ad2 23K protease binding moiety, and $R_2$ and $R_3$ are H;

$AA_3$ is alanine;

$AA_4$ is leucine;

$AA_5$ is a direct bond; and $R_4$ is absent.

89. An inhibitor of claim 74 wherein Z is a human rhinovirus 3C protease binding moiety, and $R_2$ is RCOOR' where R is —CH$_2$—;

$R_3$ is benzyl; and $AA_3$ is leucine or a direct bond.

90. An inhibitor of claim 74 wherein Z is a human rhinovirus 3C protease binding moiety, and $R_2$ is —RC(O)NR'R" where R' and R" are H or —CH$_3$; or RCOOR' where R' is —CH$_3$ or —CH$_2$CH$_3$; or X' is N and $R_2$ is —CH$_3$.

91. An inhibitor of claim 74 wherein Z is human picomain 2A protease.

92. An inhibitor of claim 81 wherein $R_3$ is —CH(OR')CH$_3$ where R' is H, alkyl or aryl.

93. An inhibitor of claim 92 wherein $R_2$ is a hydrophobic side chain.

94. An inhibitor of claim 7 wherein Z is a human picomain 2A protease binding moiety, and is $R_4$—Ala—Ala—Pro—Val—; or $R_4$—Ala—Ala—Pro—Ala—.

95. An inhibitor of claim 10 wherein Z is a protozoan protease binding moiety.

96. An inhibitor of claim 95 wherein Z is a Trypanosoma, Schistosoma or Leishmania protease binding moiety.

97. An inhibitor of claim 96 wherein $R_2$ is benzyl optionally subsituted with OH; H$_2$NC(=$^+$NH$_2$)NHCH$_2$CH$_2$CH$_2$—; —R'—C(=$^+$NH$_2$)NH$_2$; —R'—NHC(=$^+$NR")NR°; or —R'—NR"R° where R' is cycloalkyl, aryl or arylalkyl optionally substituted with one or more heteroatoms selected from N, S or O alkyl; and R" and R° are alkyl or cycloalkyl.

98. An inhibitor of claim 97 wherein $R_3$ is benzyl, (CH$_3$)$_2$CHCH$_2$— or (CH$_3$)$_2$CH—; and $AA_3$ is Phe, Leu, Pro or a direct bond.

99. An inhibitor of claim 98 wherein $R_4$ is Boc or Suc.

100. An inhibitor of claim 95 wherein Z is a Plasmodium protease binding moiety.

101. An inhibitor of claim 100 wherein $R_2$ is (CH$_3$)$_2$CH—; —CH$_2$-benzyl, benzyl or phenyl optionally substituted with hydroxyl; alkylimidazoyl; H$_2$NC(=$^+$NH$_2$)NHCH$_2$CH$_2$CH$_2$—; —R'—C(=$^+$NH$_2$)NH$_2$; —R'—NHC(=$^+$NR")NR°; or —R'—NR"R° where R' is cycloalkyl, aryl or arylalkyl optionally substituted with one or more heteroatoms selected from N, S or O alkyl; and R" and R° are alkyl or cycloalkyl.

102. An inhibitor of claim 101 wherein $R_3$ is benzyl, (CH$_3$)$_2$CHCH$_2$—, (CH$_3$)$_2$CH—, HOCH$_2$— or —CH$_2$OR'.

103. An inhibitor of claim 100 wherein Z is $R_4$—Phe—Arg—;
$R_4$—Phe—(arginine mimetic)—;
$R_4$—Val—Leu—(arginine mimetic)—;
$R_4$—Phe—Lys—;
$R_4$—Leu—hPhe—;
$R_4$—Val—Leu—Arg—;
$R_4$—Phe(e—Z)—Lys—;
$R_4$—Phe—Val—; or
$R_4$—Phe—Ser(OBzl)—.

104. An inhibitor of claim 100 wherein Z is $R_4$—Phe—$AA_1$—; or
$R_4$—Leu—$AA_1$—;

wherein $AA_1$ is optionally substituted lysine.

105. An inhibitor of claim 104 wherein $R_4$ is morpholino.

106. An inhibitor of claim 104 wherein $R_4$ is Cbz.

107. A method of inhibiting the enzymatic activity of one or more cysteine proteases comprising contacting a protease with an inhibitory amount of a compound of claim 1.

108. A method of inhibiting the enzymatic activity of one or more cysteine proteases comprising contacting a protease with an inhibitory amount of a compound of claim 10.

109. A method of inhibiting the enzymatic activity of a calpain cysteine protease comprising contacting a protease with an inhibitory amount of a compound of claim 15.

110. A method of inhibiting the enzymatic activity of a cysteine cathepsin comprising contacting the protease with an inhibitory amount of a compound of claim 24.

111. A method of inhibiting the enzymatic activity of a caspase comprising contacting the protease with an inhibitory amount of a compound of claim 52.

112. The method of claim 111 wherein the caspase is human interleukin-1β converting enzyme.

113. A method of inhibiting the enzymatic activity of a viral or microbial cysteine protease comprising contacting the protease with an inhibitory amount of a compound of claim 74.

114. The method of claim 113 wherein the cysteine protease is human coronavirus.

115. The method of claim 113 wherein the microbial cysteine protease is gingipain.

116. A method of inhibiting the enzymatic activity of a protozoan cysteine protease comprising contacting the protease with an inhibitory amount of a compound of claim 95.

117. The method of claim 116 wherein the protozoan protease is a Trypanosoma, Schistosoma or Leishmania protease.

118. The method of claim 116 wherein the protozoan protease is a Plasmodium protease.

119. A method of inhibiting the enzymatic activity of cancer procoagulant comprising contacting the protease with an inhibitory amount of a compound of claim 1.

120. A method of inhibiting the enzymatic activity of cysteine proteases associated with apoptosis in pathological states comprising contacting the proteases with an inhibitory amount of a compound of claim 1.

121. A method of inhibiting cancer cell growth or tumor progression or tumor metastasis or invasion, by inhibiting the enzymatic activity of cysteine proteases associated with such growth or progession, comprising contacting such protease with an inhibitory amount of a compound of claim 1 or 2.

122. The method of claim 121 wherein said protease is cathepsin B or cathepsin L.

123. A method of inhibiting microbial cell or viral growth or reproduction by inhibiting the enzymatic activity of cysteine proteases associated with such growth or reproduction, comprising contacting such protease with an inhibitory amount of a compound of claim 1 or 2.

124. The method of claim 123 wherein the cysteine protease is hepatitis A virus 3C proteinase.

125. The method of claim 123 wherein the cysteine protease is hepatitis C virus endopeptidase 2.

126. The method of claim 123 wherein the cysteine protease is picomain 3C rhinovirus protease.

127. The method of claim 123 wherein the cysteine protease is foot and mouth disease virus L proteinase.

128. The method of claim 123 wherein the cysteine protease is encephalomyelitis virus endopeptidase 2.

129. The method of claim 123 wherein the cysteine protease is picornain 2A protease.

130. A method of treating the symptoms associated with allergic response by inhibiting the enzymatic activity of cysteine proteases associated with such response, comprising contacting such protease with an inhibitory amount of a compound of claim 1 or 2.

131. The method of claim 130 wherein the protease is Der p I.

132. A method of treating the symptoms associated with a neurodegenerative disorder by inhibiting the enzymatic activity of cysteine proteases associated with such disease, comprising contacting such protease with an inhibitory amount of a compound of claim 1 or 2.

133. The method of claim 132 wherein the neurodegenerative disorder is Alzheimer's disease, Parkinson's disease or multiple sclerosis.

134. The method of claim 133 wherein said disorder is a result of ischemic-reperfusion injury.

135. The method of claim 134 wherein the ischemic-reperfusion injury is stroke.

136. The method of claim 134 wherein the ischemic-reperfusion injury is myocardial infarction, transplantation, vascular injury or cardiovascular collapse or shock.

137. A method of treating the symptoms associated with inflammatory and degenerative diseases by inhibiting the enzymatic activity of cysteine proteases associated with such diseases, comprising contacting such protease with an inhibitory amount of a compound of claim 1 or 2.

138. The method of claim 137 wherein the inflammatory disease is an arthridity.

139. The method of claim 138 wherein the arthridity is rheumatoid arthiritis or osteoarthritis.

140. The method of claim 137 wherein the inflammatory disease is periodontal disease.

141. The method of claim 107 wherein the compound is [2-[5-(3-methylbenzyl)-1,3,4-oxadiazolyl]carbonyl]-2-(S)-methylpropyl]-L-phenylalanamide-(3R)-(isobutyl)succinic acid.

142. The method of claim 107 wherein the compound is:

Acetyl-L-leucyl-N-[1-[2-[5-phenyl]-1,3,4-oxadiazolyl] carbonyl]-4-(guanidino)-butyl-L-leucyl amide;

Acetyl-L-leucyl-N-[1-[3-[5-methyl]-1,2,4-oxadiazolyl] carbonyl]-ethyl-L-leucyl amide;

Acetyl-L-leucyl-N-[1-[3-[5-methyl]-1,2,4-oxadiazolyl] carbonyl]-4-(guanidino)-butyl-L-leucyl amide;

Acetyl-L-tyrosinyl-L-valyl-N-[1-[2-[(5-phenyl)-1,3,4-oxadiazolyl]carbonyl]-2-carboxy-ethyl]-L-alanine amide; or Acetyl-L-Aspartyl-Valyl-N-[1-[2-[(5-phenyl)-1,3,4-oxadiazolyl] carbonyl]-2-(carboxy)-ethyl]-L-glutamyl amide.

143. The method of claim 107 wherein the compound is
(t-butoxysuccinyl)-L-valyl-N-[1-[3-[5-(3-trifluoromethylbenzyl)- 1,24-oxadiazolyl]carbonyl]-2-benzylidone]-L-prolinamide; or carboxysuccinyl-L-valyl-N-[1-[3-[5-(3-trifluoromethylbenzyl)-1,2,4-oxadiazolyllcarbonyl]-2-benzylidone]-L-prolinamide.

144. The method of claim 103 whereinthe compound is (benzyloxycarbonyl)-L-valyl-N-[1-(2-[5-(3-methylbenzyl)-1,3,4-oxadiazolyl]carbonyl)-2-(S)-methylpropyl]-L-prolinamide.

145. A method of detecting or quantifying the activity of a cysteine protease in a pure sample, mixture or a biological fluid or tissue, comprising contacting said protease with a compound of claim 1 or 2.

146. A method of purifying a cysteine protease in a sample, comprising contacting said protease with a compound of claim 1 or 2.

* * * * *